United States Patent
Fletcher et al.

(10) Patent No.: US 6,919,454 B2
(45) Date of Patent: *Jul. 19, 2005

(54) BIPHENYL-SUBSTITUTED TRIAZINES

(75) Inventors: Ian John Fletcher, Magden (CH);
Jürgen Kaschig, Frelburg (DE);
Georges Metzger, Moernach (FR);
Dieter Reinehr, Kandern (DE); Pascal Hayoz, Hofstetten (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/921,282

(22) Filed: Aug. 18, 2004

(65) Prior Publication Data
US 2005/0019281 A1 Jan. 27, 2005

Related U.S. Application Data

(60) Division of application No. 10/209,440, filed on Jul. 31, 2002, now Pat. No. 6,841,670, which is a continuation of application No. 09/848,013, filed on May 3, 2001, now Pat. No. 6,468,958, which is a division of application No. 09/383,163, filed on Aug. 25, 1999, now Pat. No. 6,255,483, which is a continuation-in-part of application No. 08/913,214, filed as application No. PCT/EP96/00945 on Mar. 6, 1996, now abandoned.

(30) Foreign Application Priority Data

Mar. 15, 1995 (CH) ............................................. 740/95
Nov. 17, 1995 (CH) ............................................. 3269/95

(51) Int. Cl.⁷ .......................... C07D 251/24; C08K 5/34
(52) U.S. Cl. ...................... 544/216; 510/513; 524/100; 8/115.59
(58) Field of Search .................... 544/216; 514/513; 524/100

(56) References Cited

U.S. PATENT DOCUMENTS

| | | | |
|---|---|---|---|
| 3,118,887 A | 1/1964 | Hardy et al. | 260/248 |
| 3,242,175 A | 3/1966 | Duennenberger et al. | 260/248 |
| 3,244,708 A | 4/1966 | Duennenberger et al. | 260/248 |
| 3,249,608 A | 5/1966 | Biland et al. | 260/248 |
| 3,444,164 A | 5/1969 | Luethi et al. | 260/248 |
| 3,544,566 A | 12/1970 | Brunetti et al. | 260/244 |
| 3,544,567 A | 12/1970 | Brunetti et al. | 260/244 |
| 3,843,371 A | 10/1974 | Piller et al. | 96/84 |
| 4,619,956 A | 10/1986 | Susi | 524/87 |
| 4,826,978 A | 5/1989 | Migdal et al. | 544/216 |
| 5,288,778 A | 2/1994 | Schmitter et al. | 524/100 |
| 5,298,067 A | 3/1994 | Valet et al. | 106/506 |
| 5,364,749 A | 11/1994 | Leppard et al. | 430/507 |
| 5,412,008 A | 5/1995 | Michaelis | 524/100 |
| 5,478,935 A | 12/1995 | Reinehr et al. | 544/180 |
| 5,597,854 A | 1/1997 | Birbaum et al. | 524/100 |
| 5,674,668 A | 10/1997 | Hagemann et al. | 430/507 |
| 6,255,483 B1 * | 7/2001 | Fletcher et al. | 544/216 |
| 6,468,958 B1 * | 10/2002 | Fletcher et al. | 510/513 |

FOREIGN PATENT DOCUMENTS

| | | |
|---|---|---|
| CH | 480 090 | * 12/1969 |
| CH | 480090 | 12/1969 |
| CH | 484695 | 1/1970 |
| CH | 484 695 | * 3/1970 |
| EP | 0165608 | 12/1985 |

(Continued)

OTHER PUBLICATIONS

Chem. Abstr. 119:213920n (1993) for EP 530135.
Chem. Abstr. 72:90534r (1970) for CH 480090.
Chem. Abstr. 119:82785x (1993) for EP 520938.
Chem. Abstr. 118:192966u (1993) for EP 506615.
Chem. Abstr. 118:104874j (1993) for EP 502816.
Chem. Abstr. 118:214256s (1993) for EP 500496.

Primary Examiner—Venkataraman Balasubramanian
(74) Attorney, Agent, or Firm—Tyler A. Stevenson

(57) ABSTRACT

Biphenyl-substituted triazines of the formula

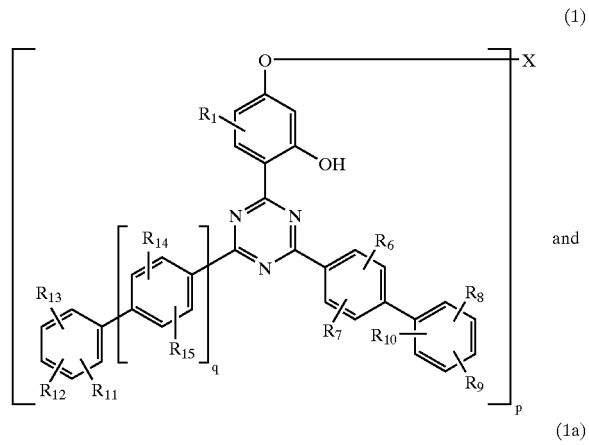

and

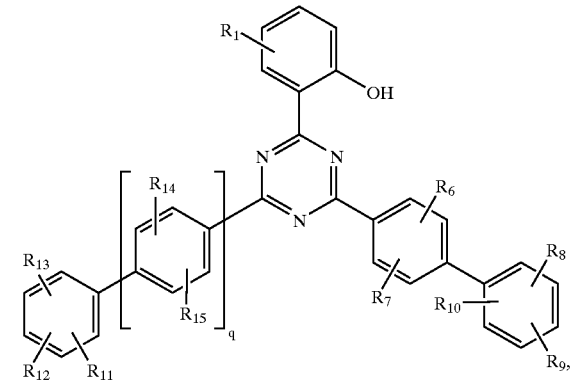

which are notable for high thermal stability, are used as stabilizers for organic polymers to counter damage thereto caused by light, oxygen and heat, as light stabilizers for textile fiber materials and as sunscreens for the human skin.

9 Claims, No Drawings

FOREIGN PATENT DOCUMENTS

| | | |
|---|---|---|
| EP | 0434608 | 6/1991 |
| EP | 0483488 | 5/1992 |
| EP | 0500496 | 8/1992 |
| EP | 0502816 | 9/1992 |
| EP | 0506615 | 9/1992 |
| EP | 0520938 | 12/1992 |
| EP | 0530135 | 3/1993 |
| EP | 648754 | 4/1995 |
| EP | 0649841 | 4/1995 |
| FR | 1494413 | 12/1967 |
| GB | 1321561 | * 6/1973 |
| GB | 2273498 | 6/1994 |
| GB | 2278115 | 11/1994 |
| GB | 2286774 | 8/1995 |
| WO | 94/05645 | 3/1994 |
| WO | 94/18278 | 8/1994 |

* cited by examiner

BIPHENYL-SUBSTITUTED TRIAZINES

This is a divisional of app. Ser. No. 10/209,440, filed Jul. 31, 2002, now U.S. Pat. No. 6,841,670, which is a continuation of app. Ser. No. 09/848,013, filed May 3, 2001, now U.S. Pat. No. 6,468,958, which is a divisional of app. Ser. No. 09/383,163, filed Aug. 25, 1999, now U.S. Pat. No. 6,255,483, which is a continuation-in-part of app. Ser. No. 08/913,214, filed Sep. 10, 1997, abandoned, which is a national stage of PCT/EP96/00945, filed Mar. 6, 1996.

The present invention relates to biphenyl-substituted triazine compounds, to processes for the preparation of these compounds, to organic material stabilized with the aid of these compounds against damage by sunlight, heat and oxygen, to the corresponding use of these compounds as stabilizers for organic material, and to their use as light stabilizers for textile fiber materials and as sunscreens for the human skin.

If it is desired to increase the light stability of an organic material, especially a coating, a light stabilizer is usually added. A class of light stabilizers which is very frequently employed comprises the UV absorbers, which protect the material by absorbing the harmful radiation via chromophores. An important group of UV absorbers is the triphenyltriazines, as are described inter alia in EP-A-434 608, EP-A-520 938, U.S. Pat. No. 4,619,956, EP-A-483 488, EP-A-500 496, EP-A-502 816 and EP-A-506 615. Some bis-resorcinyl derivatives from this group are mentioned, for example, in CH-A-480 090, CH-A-484 695, U.S. Pat. No. 3,249,608, U.S. Pat. No. 3,244,708, U.S. Pat. No. 3,843,371, U.S. Pat. No. 4,826,978, EP-A-434 608, EP-A-520 938, GB-A-2 273 498 and WO-A-94/18 278.

It has now been found that certain biphenyl-substituted triazine compounds have surprisingly high absorption in the range from 300 to 400 nm which is important for organic polymers.

The novel biphenyl-substituted triazine compounds are of the formula

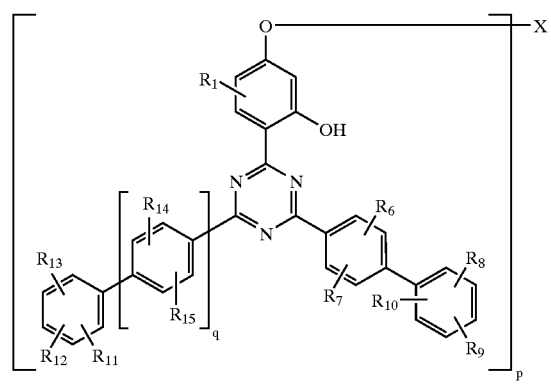

(1)

or

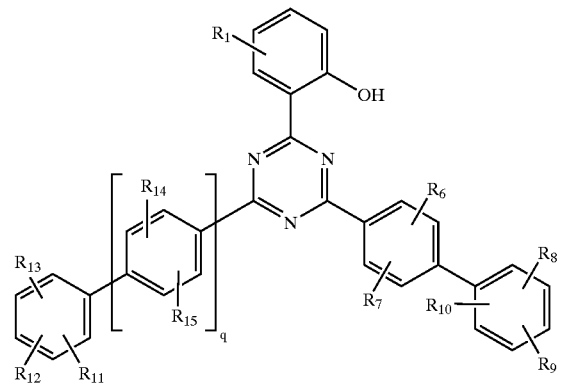

(1a)

in which $R_1$ is hydrogen; $C_1$–$C_{24}$alkyl or $C_5$–$C_{12}$cycloalkyl; or $C_1$–$C_{24}$alkyl or $C_5$–$C_{12}$cycloalkyl, which are substituted by 1 to 9 halogen atoms, —$R_4$, —$OR_5$, —$N((R_5)_2$, =$NR_5$, =O, —$CON(R_5)_2$, —$COR_5$, —$COOR_5$, —$OCOR_5$, —$OCON(R_5)_2$; —CN, —$NO_2$, —$SR_5$, —$SOR_5$, —$SO_2R_5$, —$P(O)(OR_5)_2$, a morpholinyl, piperidyl, 2,2,6,6-tetramethylpiperidyl, piperazinyl or N-methylpiperazinyl group, or combinations thereof; and/or $C_1$–$C_{24}$alkyl or $C_5$–$C_{12}$cycloalkyl which is interrupted by 1 to 6 phenylene, —O—, —$NR_5$—, —$CONR_5$—, —COO—, —OCO—, —CH($R_5$)—, —C($R_5$)$_2$— or —CO— groups or combinations thereof;

and $R_1$ is furthermore $C_2$–$C_{24}$alkenyl; halogen; —$SR_3$, $SOR_3$; $SO_2R_3$; —$SO_3H$; —$SO_3M$; or a radical of the formula

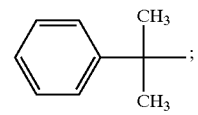

$R_3$ is $C_1$–$C_{20}$alkyl; $C_3$–$C_{18}$alkenyl; $C_5$–$C_{12}$cycloalkyl; $C_7$–$C_{15}$phenylalkyl, or $C_6$–$C_{12}$aryl which is unsubstituted or substituted by 1 to 3 $C_1$–$C_4$alkyl groups;

$R_4$ is unsubstituted $C_6$–$C_{12}$aryl; or $C_6$–$C_{12}$aryl which is substituted by 1 bis 3 halogen atoms, $C_1$–$C_8$alkyl or $C_1$–$C_8$alkoxy or combinations thereof; $C_5$–$C_{12}$cycloalkyl; unsubstituted $C_7$–$C_{15}$-phenylalkyl; or $C_7$–$C_{15}$phenylalkyl which is substituted in the phenyl ring by 1 to 3 halogen atoms, $C_1$–$C_8$alkyl, $C_1$–$C_8$alkoxy or combinations thereof or $C_2$–$C_8$alkenyl;

$R_5$ is $R_4$; hydrogen; $C_1$–$C_{24}$alkyl; or a radical of the formula

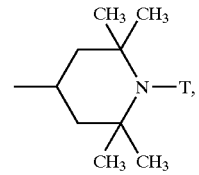

in which
T is hydrogen; $C_1$–$C_8$alkyl; $C_2$–$C_8$alkyl which is substituted by one or more hydroxyl groups or by one or more acyloxy groups; oxyl; hydroxyl; —$CH_2CN$; $C_1$–$C_{18}$alkoxy; $C_5$–$C_{12}$cycloalkoxy; $C_3$–$C_6$alkenyl; $C_7$–$C_9$phenylalkyl; $C_7$–$C_9$phenylalkyl which is substituted one, two or three times in the phenyl ring by $C_1$–$C_4$alkyl; or aliphatic $C_1$–$C_8$alkanoyl;

$R_6$ to $R_{15}$ independently of one another are hydrogen; hydroxyl; —C≡N; $C_1$–$C_{20}$alkyl; $C_1$–$C_{20}$-alkoxy; $C_7$–$C_{20}$phenylalkyl; $C_4$–$C_{12}$cycloalkyl; $C_4$–$C_{12}$cycloalkoxy; halogen; halo-$C_1$–$C_5$-alkyl; sulfonyl; carboxyl; acylamino; acyloxy; $C_1$–$C_{12}$alkoxycarbonyl; aminocarbonyl; —O—Y; or O-Z; or $R_8$ and $R_9$, together with the phenyl radical, are a cyclic radical which is interrupted by one or more oxygen or nitrogen atoms;

M is alkali metal;
p 1 or 2;
q 0 or 1;
and, if q is 0, $R_{12}$ and $R_{13}$ are not hydroxyl;
if p is 1,
X, Y and Z independently of one another are hydrogen; $C_4$–$C_{50}$alkyl which is interrupted by one or more oxygen atoms and/or substituted by one or more hydroxyl groups;

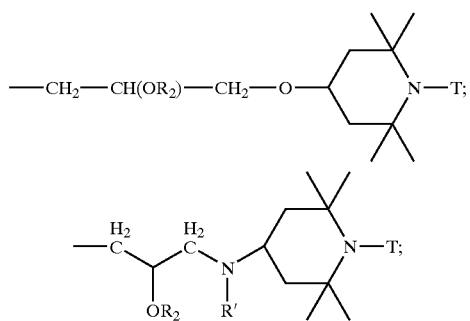

$C_4$–$C_{12}$cycloalkyl which is substituted by $R_2$; —$OR_2$-substituted $C_4$–$C_{12}$cycloalkyl; —CH(($CH_2$)$_n$—$R_2$)—CO—O—($CH_2$)$_m$—R'$_2$; —CH(($CH_2$)$_n$—$R_2$)—CO—(NR')—($CH_2$)$_m$—R'$_2$;

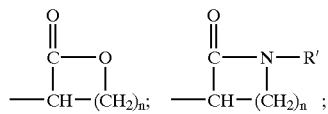

—CO—($CH_2$)$_n$—$R_2$; —CO—O—($CH_2$)$_n$—$R_2$, —$CH_2$—CH(—O(CO)—$R_2$)—R'$_2$, —CO—NR'—($CH_2$)$_n$—$R_2$; $C_6$–$C_{12}$aryl; allyl; $C_4$–$C_{20}$alkenyl which is unsubstituted or is interrupted by one or more oxygen atoms; $C_4$–$C_{12}$cycloalkenyl which is unsubstituted or is substituted by one or more oxygen atoms; $C_3$–$C_{20}$alkynyl; or $C_6$–$C_{12}$cycloalkynyl;

$R_2$ and R'$_2$ independently of one another are $R_x$ if attached to a carbon atom and are $R_y$ if attached to an atom other than carbon;
n 0 to 20;
m 0 to 20;
and, if p is 2,
Y and Z independently of one another are as defined for when p is 1; and
X is $C_2$–$C_{12}$alkylene; —CO—($C_2$–$C_{12}$alkylene)—CO—; —CO-phenylene-CO—; CO-biphenylene-CO—; CO—O—($C_2$–$C_{12}$alkylene)—O—CO—; —CO—O-phenylene-O—CO—; —CO—O-biphenylene-O—CO—; —CO—NR'—($C_2$–$C_{12}$alkylene)—NR'—CO—; —CO—NR'-phenylene-NR'—CO—; —CO—NR'-biphenylene-NR'—CO—; —$CH_2$—CH(OH)—$CH_2$—; —$CH_2$—CH(O$R_2$)—$CH_2$—; —$CH_2$—CH(OH)—$CH_2$—O-D-O—$CH_2$—CH(OH)—$CH_2$; —$CH_2$—CH(O$R_2$)—$CH_2$—O-D-O—$CH_2$—CH(O$R_2$)—$CH_2$—;

D is $C_2$–$C_{12}$alkylene; $C_4$–$C_{50}$alkylene which is interrupted by one or more oxygen atoms; phenylene; biphenylene or phenylene-E-phenylene;

E is —O—; —S—; —$SO_2$—; —$CH_2$—; —CO—; or —C($CH_3$)$_2$—;

$R_x$ is hydrogen; hydroxyl; $C_1$–$C_{20}$alkyl; $C_4$–$C_{12}$cycloalkyl; $C_1$–$C_{20}$alkoxy; $C_4$–$C_{12}$cycloalkoxy; $C_4$–$C_{12}$cycloalkyl or $C_4$–$C_{12}$cycloalkoxy which is interrupted by one or more oxygen atoms; $C_6$–$C_{12}$aryl; hetero-$C_3$–$C_{12}$aryl; —O$R_z$; NH$R_z$; $R_z$; CONR'R''; allyl; $C_2$–$C_{20}$alkenyl; $C_4$–$C_{12}$-cycloalkenyl which is uninterrupted or interrupted by one or more oxygen atoms; $C_3$–$C_{20}$-alkynyl; or $C_6$–$C_{12}$cycloalkynyl;

$R_y$ is hydrogen; $C_1$–$C_{20}$alkyl; $C_4$–$C_{12}$cycloalkyl which is uninterrupted or interrupted by one or more oxygen atoms; $C_6$–$C_{12}$aryl; hetero-$C_3$–$C_{12}$aryl; $R_z$; allyl; $C_2$–$C_{20}$alkenyl; $C_4$–$C_{12}$-cycloalkenyl which is uninterrupted or is interrupted by one or more oxygen atoms; $C_3$–$C_{20}$alkynyl; or $C_6$–$C_{12}$cycloalkynyl;

$R_z$ is —COR'; —COOR'; —CONR'R''; —CO—CH=$CH_2$; —CO—C($CH_3$)=$CH_2$;

R' and R'' independently of one another are hydrogen; $C_1$–$C_{20}$alkyl; $C_4$–$C_{50}$alkyl which is interrupted by one or more oxygen atoms; $C_4$–$C_{12}$cycloalkyl which is uninterrupted or interrupted by one or more oxygen atoms; $C_2$–$C_{20}$alkenyl which is unsubstituted or is interrupted by one or more oxygen atoms; or $C_6$–$C_{12}$aryl.

The radicals $R_x$, $R_y$, R' and R'' can independently of one another be substituted by hydroxyl, —$NH_2$, —NHR', —NR'R'', halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$cycloalkynyl, $C_6$–$C_{12}$aryl, acylamine, acyloxy, sulfonyl, carboxyl, (meth)acryloxy, (meth)acrylamino,

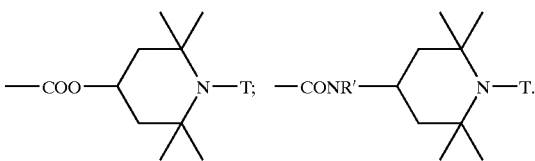

The above-mentioned radicals can also constitute isomer mixtures from the definitions given. When q is 0, compounds are preferred wherein none of $R_6$ to $R_{15}$ is OH or allyloxy, especially wherein none is OH or alkenyloxy.

Alkyl is branched or unbranched alkyl, such as methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl.

$C_1$–$C_{20}$alkoxy comprises straight-chain or branched radicals such as, for example, methoxy, ethoxy, propoxy, butoxy, pentyloxy, hexyloxy, heptyloxy, octyloxy, isooctyloxy, nonyloxy, undecyloxy, dodecyloxy, tetradecyloxy or pentadecyloxy, hexadecyloxy, heptadecyloxy, octadecyloxy, nonadecyloxy or eicosyloxy.

Phenylalkyl is alkyl which is substituted by phenyl. $C_7-C_{20}$phenylalkyl, for example, comprises benzyl, α-methylbenzyl, α,α-dimethylbenzyl, phenylethyl, phenylpropyl, phenylbutyl, phenylpentyl, phenylhexyl, phenylheptyl, phenyloctyl, phenylnonyl, phenyldecyl, phenyldodecyl or phenyltetradecyl.

Halogen is —F, —Cl, —Br or —I; preference is given to —F or —Cl, especially —Cl.

$C_4-C_{12}$cycloalkyl is for example cyclobutyl, cyclopentyl, cycloheptyl, cyclooctyl, cyclononyl, cyclodecyl, cycloundecyl, cyclodocecyl and, in particular cyclohexyl.

Examples of $C_4-C_{12}$cycloalkyl interrupted by one or more oxygen atoms are tetrahydrofuryl, 1-oxa-4-cyclohexyl and 1,3-dioxa-4-cyclohexyl.

Within the scope of the definitions given alkenyl includes allyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl and n-octadec-4-enyl, inter alia. $C_2-C_{20}$alkenyl is most preferably allyl or vinyl when bonded to a carbon atom, and allyl when bonded to a non-carbon atom.

Acyl is the residue of an aliphatic, cycloaliphatic or aromatic carboxylic acid preferably of 2–20 carbon atoms. Preferred are $C_2-C_{18}$alkanoyl, $C_3-C_8$alkenoyl, or the residue of a $C_7-C_{12}$phenyl carboxylic acid like benzoic acid, methylbenzoic acid, phenylacetic acid or cinnamic acid.

$C_2-C_{18}$alkanoyl is for example acetyl, propionyl, acryloyl, methacryloyl or benzoyl.

$C_3-C_8$alkenoyl is for example acryloyl or methacryloyl.

$C_5-C_{12}$cycloalkenyl is for example 2-cyclopenten-1-yl, 2,4-cyclopentadien-1-yl-, 2-cyclohexen-1-yl, 2-cyclohepten-1-yl or 2-cyclooczten-1-yl.

$C_4-C_{12}$cycloalkoxy is for example cyclobutyloxy, cyclopentyloxy, cyclohexyloxy, cycloheptyloxy, cyclooctyloxy, cyclononyloxy, cyclodecyloxy, cycloundecyloxy, cyclododecyloxy, especially cyclohexyloxy.

Particular examples of $C_6-C_{12}$aryl are phenyl, naphthyl and biphenyl.

Hetero-$C_3-C_{12}$aryl is preferably pyridyl, pyrimidinyl, triazinyl, pyrrolyl, furyl, thiophenyl or quinolyl.

A cyclic radical formed by $R_{11}$ and $R_{12}$ together with the phenyl radical is mainly one containing 2–4 carbon atoms; an example is 3,4-dimethylenedioxyphenyl.

Preferred compounds according to the invention are of the formula

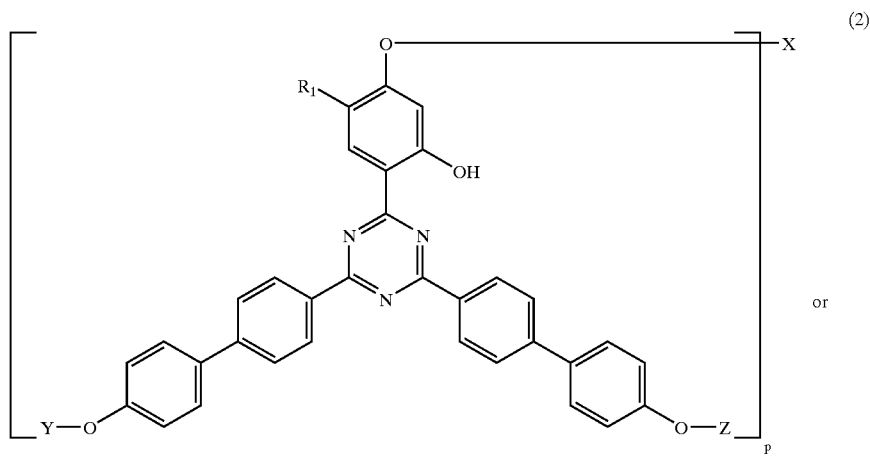

(2)

or

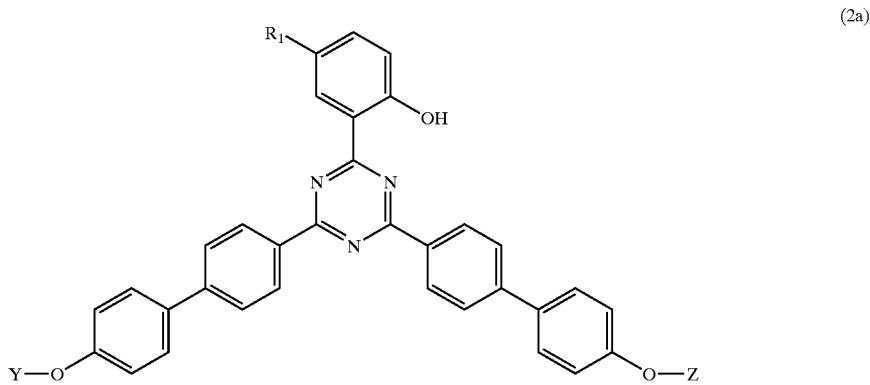

(2a)

and in particular of the formula

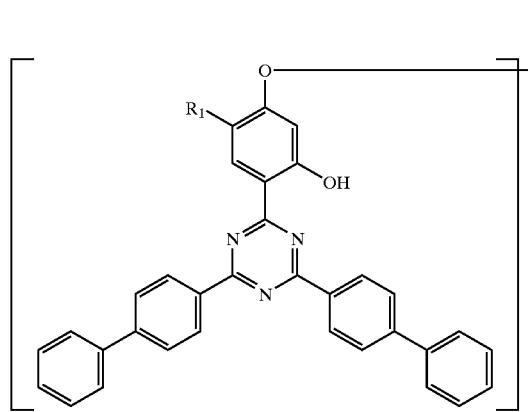

(3)

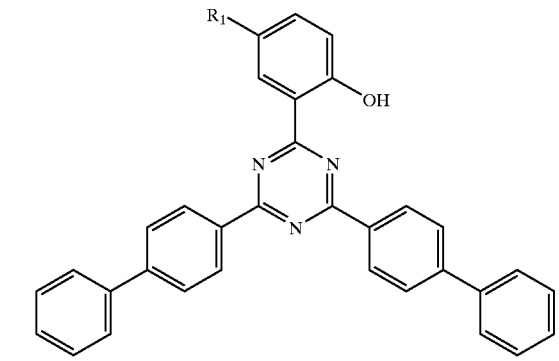

(3a)

in which $R_1$, X, Y, Z and p are as defined for formula (1).

Among the compounds of the formula (3) or (3a), preference is given to those in which X is $((CH_2)_m-CH_2-O-)_n-R_y$; $-(CH_2)_n-R_x$; $-CH_2-CH(OH)-CH_2-O-(CH_2)_n-R_x$;

$R_x$ is hydrogen; hydroxyl; $C_1-C_{20}$alkyl; or $C_4-C_{12}$cycloalkyl;

$R_y$ is hydrogen; or $C_1-C_{20}$alkyl; or $C_4-C_{12}$cycloalkyl;

m is 0 to 20;

n is 0 to 20;

p is 1;

and $R_1$ is as defined in formula 1.

Very particular preference attaches to triazine compounds of the formulae (1) to (3) and (1a) to (3a) in which X, Y and Z independently of one another are hydrogen, $-((CH_2)_m-CH_2-O-)_n-R_2$; $-(CH_2-CH((CH_2)_m-R_2)-O-)_n-R'_2$; $-(CH((CH_2)_m-R_2)-CH_2-O-)_n-R'_2$; $-(CH_2)_n-R_2$; $-CH_2-CH(OH)-CH_2-O-(CH_2)_n-R_2$; $-CH_2-CH(OR_2)-CH_2-O-(CH_2)_n-R'_2$; $-CH_2-CH(OH)-CH_2-O-(CH_2)_nOR_2$; or $-CH_2-CH(OR_2)-CH_2-O-(CH_2)_n-OR'_2$.

Further preferred compounds are those of the formula

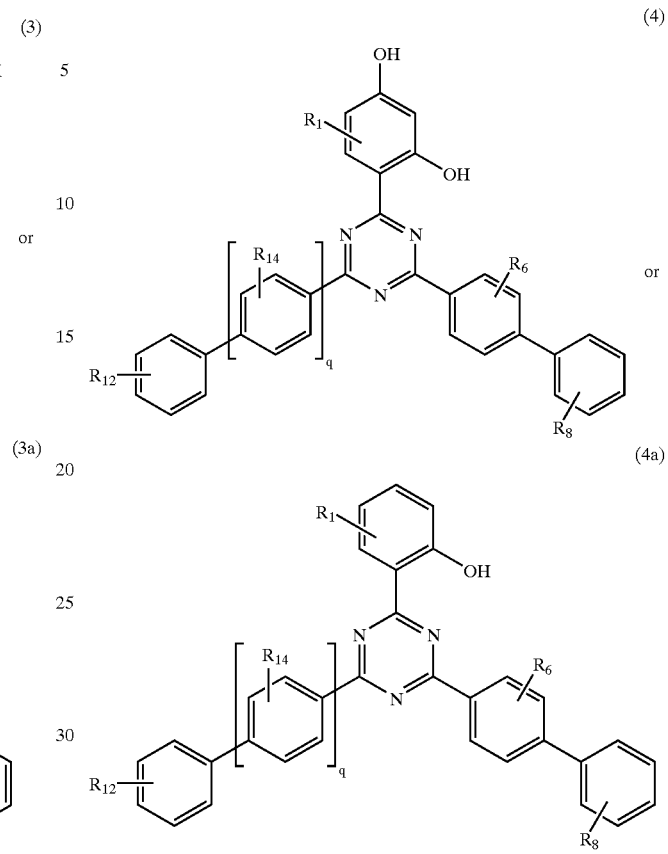

(4)

(4a)

in which $R_1$ is hydrogen; $C_1-C_{20}$alkyl; $C_1-C_{20}$alkoxy; or halogen;

$R_{14}$ is hydrogen; $C_1-C_{20}$alkyl; $C_1-C_{20}$alkoxy; phenyl-$C_1-C_{20}$alkoxy; or halogen;

$R_{12}$ is hydrogen; $C_1-C_{20}$alkyl; $C_1-C_{20}$alkoxy; or halogen;

$R_6$ and $R_8$, independently of one another are hydrogen; $C_1-C_{20}$alkyl; $C_1-C_{20}$alkoxy, or halogen; and q is 0 or 1.

Particularly preferred are those compounds of the formula (4a) in which $R_1$ is hydrogen; $C_1-C_{20}$alkyl; or $C_1-C_{20}$alkoxy;

$R_{13}$, $R_{14}$, $R_{15}$ and $R_{16}$ are hydrogen; and q is 0 or 1.

The compounds of the formulae (1) to (4) and (1a) to (4a) are novel compounds; examples of the novel compounds include 2-(2-hydroxyphenyl)-4-phenyl-6-(4-biphenyl)-1,3,5-triazine, 2-(2,4-dihydroxyphenyl)-4,6-bis(4-biphenyl)-1,3,5-triazine, 2-(2-hydroxy-4-hexyloxyphenyl)-4,6-bis(4-biphenyl)-1,3,5-triazine, 2-(2,4-dihydroxyphenyl)-4,6-bis(4-biphenyl)-1,3,5-triazine, 2-[2-hydroxy-4-(2-hydroxy-3-butyloxypropyloxy)phenyl]-4,6-bis(4-biphenyl)-1,3,5-triazine, 2-(2-hydroxy-4-octyloxyphenyl)-4,6-bis(4-biphenyl)-1,3,5-triazine, 2-[2-hydroxy-4-(2-hydroxy-3-dodecyloxypropyloxy)phenyl]-4,6-bis(4-biphenyl)-1,3,5-triazine, 2-[2-hydroxy-4-(2-hydroxy-3-tridecyloxypropyloxy)phenyl]-4,6-bis(4-biphenyl)-1,3,5-triazine, 2-(2-hydroxy-4-methoxyphenyl)-4-(2,4-dimethoxyphenyl)-phenyl-6-(4-biphenyl)-1,3,5-triazine, 2,4-bis(2-hydroxyphenyl)-6-(4-biphenyl)-1,3,5-triazine, 2-(2-hydroxyphenyl)-4-(2-methoxyphenyl)-6-(4-biphenyl)-

1,3,5-triazine, 2-(2-hydroxyphenyl)-4-(4-methoxyphenyl)-6-(4-biphenyl)-1,3,5-triazine; or 2-(2-hydroxy-4-methoxyphenyl)-4-6-bis(4-biphenyl)-1,3,5-triazine.

The novel compounds of the formulae (1) to (4) and (1a) to (4a) can be prepared in various ways.

For example, these compounds can be prepared in accordance with or in analogy to one of the methods indicated in EP-A-434 608 or in the publication by H. Brunetti and C. E. Lüthi, Helv. Chim. Acta 55, 1566 (1972), by Friedel-Crafts Addition of Halotriazines onto appropriate phenols. This may be followed by further reaction in accordance with known methods to give compounds of the formulae (1) to (4) and (1a) to (4a). Such reactions and methods are described, for example, in EP-A-434 608, page 15, line 11 to page 17, line 1.

The novel compounds can also be prepared from the corresponding benzamidine compounds of the formula

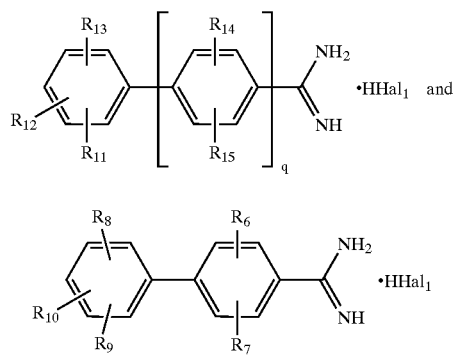

(5)

(6)

with a salicylic compound of the formula

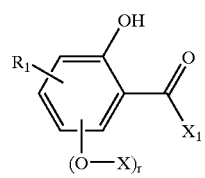

(7)

to give the triazine compound of the formula (1), where $Hal_1$ is halogen;
r is 0 or 1;
$X_1$ is halogen or $-OR_{50}$;
$R_{50}$ is $C_1$–$C_3$alkyl; and
$R_1$, $R_6$, $R_7$, $R_8$, $R_9$, $R_{10}$, $R_{11}$, $R_{12}$, $R_{13}$, $R_{14}$, $R_{15}$, q and X are as defined for formula (1).

Analogous reactions are described, for example, in EP-A-0 649 841.

The novel compounds of the formula (1) or (1a) can also be prepared by dehydrogenating the corresponding dihydrotriazine compound of the formula

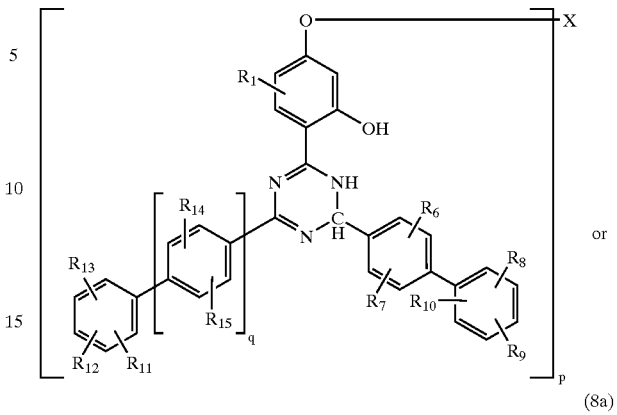

(8)

(8a)

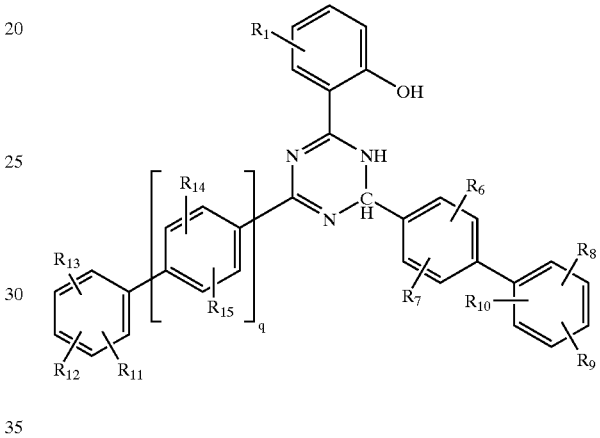

in which $R_1$, $R_6$, $R_7$, $R_8$, $R_9$, $R_{10}$, $R_{11}$, $R_{12}$, $R_{13}$, $R_{14}$, $R_{15}$, X, p and q are as defined for formula (1).

An example of the dehydrogenating agents which can be employed is chloranil. The dehydrogenation of dihydrotriazine compounds to give 1,3,5-triazines using chloranil is known, for example, from Khim. Geteritsikl. Soedin. (2), pp.350–353 (1969).

Other dehydrogenating agents which can be used for the present process are reducing agents which are known per se, for example dithionites, pyrosulfates, sulfites and thiosulfites, but which in this case act as oxidizing agents. This preparation variant is preferably carried out using sodium bisulfite or sodium dithionite. This process is described, for example, in EP-A-0 648 754.

The dihydrotriazines of the formulae (8) and (8a) are novel compounds. The invention additionally relates to these novel compounds.

The novel dihydrotriazine compounds, disubstituted by biphenyl, of the formula (8) or (8a), i.e. those for which q is 1 and p is 1 in formula (8) or (8a), are prepared by, for example, reacting the benzamidine compounds of the formula (5) and (6) with one mole of an α-hydroxybenzaldehyde of the formula

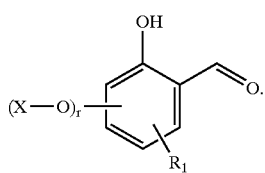

(9)

$R_1$ and X are as defined for formula (1); and
r is 0 or 1.

The novel biphenyl-substituted triazine compounds can also be prepared from the corresponding benzoxazinones of the formula

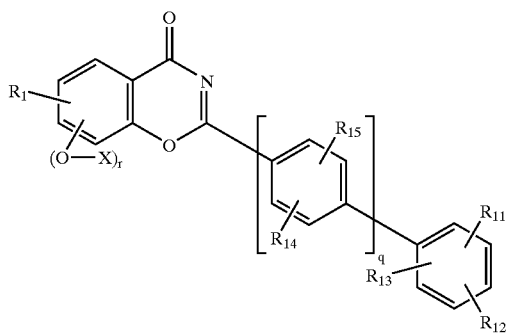

(10)

and a benzamidine compound of the formula (6).

In formula (10), $R_1$, $R_{11}$, $R_{12}$, $R_{13}$, $R_{14}$, $R_{15}$, q and X are as defined for formula (1); and
r is 0 or 1.

The reaction is generally carried out in unsubstituted or substituted $C_1$–$C_5$ alcohols, for example methylcellosolve, at a temperature from 0 to 100° C., preferably from 40 to 80° C. In general, at least the calculated quantity of a base is added in order to neutralize the acid which forms during the reaction. Bases which can be used include both organic and inorganic compounds, for example alkali metal hydroxide, especially sodium hydroxide or potassium hydroxide solution; aqueous ammonia solution; ammonia gas; alkali metal carbonate, especially sodium carbonate or potassium carbonate; sodium acetate; tertiary amines, such as pyridine or trialkylamines, especially triethylamine, N,N-dimethylcyclohexylamine, N,N-dimethylaniline; alkali metal alkylates, especially sodium methylate and potassium methylate or potassium tert-butylate.

The benzoxazinone compounds of the formula (10) are novel compounds. The present invention additionally relates to these compounds.

The novel benzoxazinone compounds of the formula (10) are accessible, for example, by acid-catalyzed cyclization of salicylamides of the formula

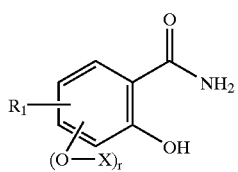

(11)

The synthesis can be carried out as a one-pot reaction by reacting the salicylamide with the carbonyl halide of the formula

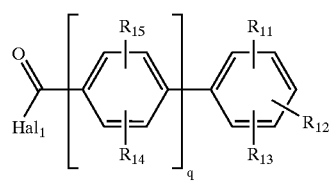

(12)

in, for example, boiling aromatic solvents, for example xylene or toluene. The reaction time in this case is from 1 to 10 hours, preferably from 2 to 4 hours.

In formulae (11) and (12) $R_1$, $R_{11}$, $R_{12}$, $R_{13}$, $R_{14}$, $R_{15}$, q, r, X and $Hal_1$ are as defined.

In analogy to the literature as represented by H. J. Kabbe, K. Eiter and F. Möller, Liebigs Ann. Chem. 704, 140–143, (1967) it is possible to prepare 2-amino-4,6-bis(4-biphenyl)-1,3,5-triazine of the formula

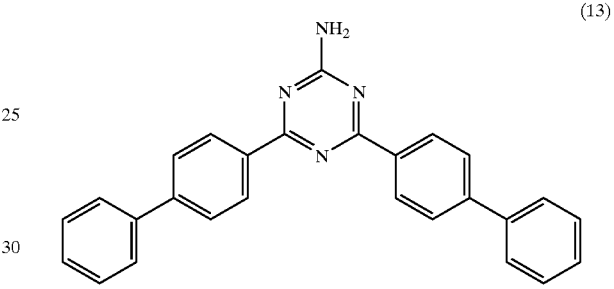

(13)

starting from 4-biphenylnitrile and a guanidine salt. The amino group can then be hydrolyzed with sodium hydroxide solution to the hydroxyl group. Subsequent reaction of $SOCl_2$ gives the compound of the formula (114) (Example 14), which can then be reacted as described to give the compound of the formula (115) (Example 15).

The novel biphenyl-substituted triazine compounds are very good UV absorbers which are particularly notable for high thermal stability. They are therefore used as stabilizers for organic polymers, especially coating materials, against damage thereto by light, oxygen and heat, and as light stabilizers for textile fiber materials.

Particular advantages of the novel biphenyl-substituted compounds include their surprisingly high absorption in the 300 to 400 nm region of the electromagnetic spectrum. Another surprising finding is that the behaviour of the solubility and melting points of the novel compounds is, despite the large conjugated aromatic system, similar to that of the solubility and melting points of comparable compounds from the prior art. Material stabilized with the compounds according to the invention features outstanding resistance to the effects of weathering and light, and outstanding photostability of the incorporated stabilizer.

The materials to be stabilized can for example be oils, fats, waxes, cosmetics or biocides. A particularly interesting application is in polymeric materials as are present in plastics, rubbers, paints and other coating materials, photographic material or adhesives. Examples of polymers and other substrates which can be stabilized in this way are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for example of cyclopentene or norbornene; furthermore polyethylene (which optionally can be crosslinked), for example high density polyethylene (HDPE), polyethylene of high density and high molecular mass (HDPE-HMW), polyethylene of high density and ultra-high molecular mass (HDPE-UHMW), medium density polyethylene (MDPE), low density polyethylene (LDPE), linear low density polyethylene (LLDPE), branched low density polyethylene (BLDPE).

Polyolefins, i.e. polymers of monoolefins exemplified in the preceding paragraph, in particular polyethylene and polypropylene, can be prepared by different, and especially by the following, methods:

a) radical polymerization (normally under high pressure and at elevated temperature)

b) catalytic polymerization using a catalyst that normally contains one or more metals of group IVb, Vb, VIb or VIII of the Periodic Table. These metals usually have one or more ligands, such as oxides, halides, alcoholates, esters, ethers, amines, alkyls, alkenyls and/or aryls that may be either π- or σ-coordinated. These metal complexes may be in the free form or fixed on substrates, for example on activated magnesium chloride, titanium(III) chloride, alumina or silicon oxide. These catalysts may be soluble or insoluble in the polymerization medium. The catalysts can be activated by themselves in the polymerization or further activators may be used, for example metal alkyls, metal hydrides, metal alkyl halides, metal alkyl oxides or metal alkyloxanes, the metals being elements of groups Ia, IIa and/or IIIa of the Periodic Table. The activators may be modified, for example, with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/lisoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned under 1), for example polypropylene/ethylene-propylene copolymers, LDPE/ethylene-vinyl acetate copolymers, LDPE/ethylene-acrylic acid copolymers, LLDPE/ethylene-vinyl acetate copolymers, LLDPE/ethylene-acrylic acid copolymers and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene poly-(p-methylstyrene), poly-(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, as well as mixtures thereof with the copolymers mentioned under 6), for example the copolymer mixtures known as ABS, MBS, ASA or AES polymers.

8. Halogen-containing polymers such as polychloroprene, chlorinated rubber, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride; polyvinylidene fluoride; as well as copolymers thereof such as vinyl chloride/vinylidene chloride, vinyl chloride/vinyl acetate or vinylidene chloride/vinyl acetate.

9. Polymers derived from α,β-unsaturated acids and derivatives thereof such as polyacrylates and polymethacrylates, polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

11. Polymers derived from unsaturated alcohols and amines of the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in point 1.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain comonomers, for example ethylene oxide; polyacetals modified with thermoplastic polyurethanes, acrylates or MBS.

14. Polyphenylene oxides and sulfides, and mixtures thereof with styrene polymers or polyamides.

15. Polyurethanes derived from hydroxyl-terminated polyethers, polyesters and polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides starting from m-xylene, diamine and adipic acid; polyamides prepared from hexamethylenediamine and isophthalic and/or terephthalic acid and with or without an elastomer as modifier, for example poly-2,4,4-trimethylhexamethylene terephthalamide or poly-m-phenylene isophthalamide. Block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol. As well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalates and polyhydroxybenzoates, as well as block polyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, urea or melamine on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example from epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, for example products of bisphenol A diglycidyl ethers, bisphenol F diglycidyl ethers, which are crosslinked by means of customary hardeners, for example anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and derivatives.

28. Blends of the aforementioned polymers (polyblends), for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The invention therefore also relates to a composition comprising
(A) an organic material which is sensitive to damage by light, oxygen and/or heat, and
(B) as stabilizer, a compound of the formula (1) or (1a).

The invention also relates to a process for stabilizing organic material against damage by light, oxygen and/or heat, which comprises adding thereto, as stabilizer, a compound of the formula (1) or (1a), and to the use of the compound of the formula (1) or (1a) for stabilizing organic material.

The amount of the stabilizer to be used depends on the organic material to be stabilized and on the intended use of the stabilized material. In general, the novel composition comprises from 0.01 to 15 parts by weight, in particular from 0.05 to 10 parts by weight, especially from 0.1 to 5 parts by weight, of the stabilizer (component B) per 100 parts by weight of component (A).

The stabilizer (component (B)) can also be a mixture of two or more compounds of the formulae (1) and (1a). In addition to the novel compounds, the novel compositions can also comprise other stabilizers or other additives, for example antioxidants, further light stabilizers, metal deactivators, phosphites or phosphonites. Examples of these stabilizers are the following:

1. Antioxidants 1.1. Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or are branched in the side chain, such as, for example, 2,6-di-nonyl-4-methylphenol, 2,4-dimethyl-6-(1-methylundec-1-yl)-phenol, 2,4-dimethyl-6-(1-methylheptadec-1-yl)-phenol, 2,4-dimethyl-6-(1-methyltridec-1-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4-thiobis(3,6-di-sec-amylphenol), 4,4-bis(2,6-dimethyl-4-hydroxyphenyl)-disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'- ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl 4-hydroxy-3,5-dimethylbenzylmercaptoacetate, tridecyl 4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl) sulfide, isooctyl 3,5-di-tert-butyl-4-hydroxybenzylmercaptoacetate.

1.8. Hydroxybenzylated malonates, for example dioctadecyl 2,2-bis(3,5-di-tert-butyl-2-hydroxybenzyl)malonate, di-octadecyl 2-(3-tert-butyl-4-hydroxy-5-methylbenzyl)malonate, di-dodecylmercaptoethyl-2,2-bis(3,5-di-tert-butyl-4-hydroxybenzyl)malonate, di-[4-(1,1,3,3-tetramethylbutyl)phenyl]2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)-isocyanurat, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.11. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

1.18. Ascorbic acid (Vitamin C).

1.19. Aminic antioxidants, for example N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclo-hexyl-N'-phenyl-p-phenylenediamine, 4-(p-toluene-sulfonamido)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, di-(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-di-[(2-methylphenyl)amino]ethane, 1,2-di-(phenylamino)propane, o-tolyl)biguanide, di-[4-(1',3'-dimethylbutyl)phenyl]amine, tert-octylated N-phenyl-1-naphthylamine, a mixture of mono- and dialkylated tert-butyl-tert-octyldiphenylamines, a mixture of mono- and dialkylated nonyldiphenylamines, a mixture of mono- and dialkylated dodecyldiphenylamines, a mixture of mono- and dialkylated isopropylisohexyldiphenylamines, mixtures of mono and dialkylated tert-butyldiphenylamines, 2,3-dihydro-3,3-dimethyl-4H-1,4-benzothiazine, phenothiazine, a mixture of mono and dialkylated tert-butyl-tert-octyl phenothiazines, a mixture of mono and dialkylated tert-octylphenothiazines, N-allylphenothiazine, N,N,N,N-tetraphenyl-1,4-diaminobut-2-ene, N,N-bis(2,2,6,6-tetramethylpiperid-4-yl) hexamethylenediamine, bis(2,2,6,6-tetramethylpiperid-4-yl) sebacate, 2,2,6,6-tetramethylpiperidin-4-one, 2,2,6,6-tetramethylpiperidin-4-ol.

2. UV-absorbers and Light Stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)-benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl)-benzotriazole, a mixture of 2-(3-tert-butyl-2'-hydroxy-5'-(2-octyloxycarbonylethyl)phenyl)-5-chlorobenzotriazole, 2-(3-tert-butyl-5-[2-(2-ethylhexyloxy)-carbonylethyl]-2'-hydroxyphenyl)-5-chlorobenzotriazole, 2-(3-tert-butyl-2'-hydroxy-5-(2-methoxycarbonylethyl) phenyl)-5-chlorobenzotriazole, 2-(3'-tert-butyl-2-hydroxy-5-(2-methoxycarbonylethyl)phenyl)-benzotriazole, 2-(3-tert-butyl-2-hydroxy-5-(2-octyloxycarbonylethyl)phenyl) benzotriazole, 2-(3-tert-butyl-5-[2-(2-ethylhexyloxy) carbonylethyl]-2-hydroxyphenyl)benzotriazole, 2-(3-dodecyl-2-hydroxy-5-methylphenyl)benzotriazole, and 2-(3-tert-butyl-2-hydroxy-5-(2-isooctyloxycarbonylethyl) phenylbenzotriazole, 2,2-methylenebis[4-(1,1,3,3-tetramethylbutyl)-6-benzotriazol-2-ylphenol]; the transesterification product of 2-[3-tert-butyl-5-(2-methoxycarbonylethyl)-2-hydroxyphenyl]benzotriazole with polyethylene glycol 300; [R—CH$_2$CH—COO(CH$_2$)$_3$]$_{\overline{2}}$ where R=3-tert-butyl-4-hydroxy-5-2H-benzotriazol-2-ylphenyl.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted and unsubstituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate or isooctyl α-cyano-β,β-diphenylacrylate, methyl α-carbomethoxycinnamate, methyl α-cyano-β-methyl-p-methoxycinnamate or butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl esters, such as of the methyl or ethyl ester, of 4-hydroxy-3,5-di-tert-butylbenzylphosphonic acid, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl)sebacate, bis(2,2,6,6-tetramethylpiperid-4-yl)succinate, bis(1,2,2,6,6-pentamethylpiperid-4-yl)sebacate, bis(1-octyloxy-2,2,6,6-tetramethylpiperid-4-yl)sebacate, bis(1,2,2,6,6-pentamethylpiperidyl)n-butyl 3,5-di-tert-butyl-4-hydroxybenzylmalonate, the condensate of 1-hydroxyethyl-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2, 5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, the condensate of N,N'-bis(2,2,6,6,-tetramethyl-4-piperidyl)-hexamethylenediamine and 4-cyclohexylamino-2,6-dichloro-1,3,5-triazine, the condensate of 1,2-bis(3-aminopropylamino)ethane and 2,4,6-trichloro-1,3,5-triazine, and also 4-butylamino-2,2,6,6-tetramethylpiperidine (CAS Reg. No. [136504-96-6]); N-(2, 2,6,6-tetramethyl-4-piperidyl)-n-dodecylsuccinimide, N-(1, 2,2,6,6-pentamethyl-4-piperidyl)-n-dodecylsuccinimide, 2-undecyl-7,7,9,9-tetramethyl-1-oxa-3,8-diaza-4-oxospiro [4.5]decane, the reaction product of 7,7,9,9-tetramethyl-2-cycloundecyl-1-oxa-3,8-diaza-4-oxospiro[4.5]decane and epichlorohydrin.

2.7. Oxalamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butoxanilide and mixtures of o- and p-methoxy disubstituted oxanilides and mixtures of o- and p-ethoxy disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4- propyloxyphenyl)-6-(2,4-dimethylphenyl)-1,3,5-triazine, 2-(2-hydroxy-4-octyloxyphenyl)-4,6bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)-phenyl]-4,6-bis(2,4-dimethylphenyl)-1,3,5-triazine, 2-[4-(dodecyloxytridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine.

3. Metal deactivators, for example, N,N'-diphenyloxalamide, N-salicylal-N'-salicyloyl hydrazine, N,N'-bis(salicyloyl)hydrazine, N,N'-bis(3,5-di-tert-butyl-4-hydroxyphenyl-propionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,6-di-tert-butyl-4-methylphenyl)pentaerythritol diphosphite, bisisodecyloxypentaerythritol diphosphite, bis(2,4-di-tert-butyl-6-methylphenyl)pentaerythritol diphosphite, bis-(2,4,6-tri-tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenzo[d,g]-1,3,2-dioxaphosphocin, 6-fluoro-2,4,8,10-tetra-tert-butyl-12-methyl-dibenzo[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine from hydrogenated tallow fatty amines.

6. Nitrones, for example N-benzyl-alpha-phenyl nitron, N-ethyl-alpha-methyl nitron, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecyl nitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrones derived from N,N-dialkylhydroxylamines prepared from hydrogenated tallow fatty amines.

7. Thio synergistic agents, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, stearate, magnesium behenate, magnesium stearate, sodium ricinoleate, and potassium palmitate, antimony pyrocatecholate or tin pyrocatecholate.

11. Nucleating agents, for example inorganic substances, such as talc, metal oxides such as titanium oxide or magnesium oxide, phosphates, carbonates or sulfates of, preferably, alkaline earth metals; organic compounds, such as mono- or polycarboxylic acids and salts thereof, for example 4-tert-butylbenzoic acid, adipic acid, diphenylacetic acid, sodium succinate or sodium benzoate; and polymeric compounds, for example ionic copolymers ("ionomers").

12. Fillers and reinforcing agents, for example calcium carbonate, silicates, glass fibers, asbestos, talc, kaolin, mica, barium sulfate, metal oxides and hydroxides, carbon black, graphite, wood flour and flours or fibers from other natural products, synthetic fibers.

13. Other additives, for example plasticizers, lubricants, emulsifiers, pigments, rheological additives, catalysts, levelling assistants, optical brighteners, flameproofing agents, antistatic agents and blowing agents.

14. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 or EP-A-0 591 102 or 3-[4-(2-acetoxyethoxy-phenyl]-5,7-di-tert-butyl-benzofuran-2-one, 5,7-di-tertbutyl-3-[4-(2-stearoyloxy-ethoxy)-phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The type and amount of the further stabilizers added is determined by the type of substrate to be stabilized and on its intended use; frequently, from 0.1 to 5% by weight, based on the polymer to be stabilized, are used.

The novel stabilizers can with particular advantage be employed in compositions in which component (A) is a synthetic organic polymer, especially a thermoplastic polymer, a binder for coatings, for example paints, or a photographic material. Examples of suitable thermoplastic polymers are polyolefins and polymers comprising heteroatoms in the main chain. Preference is also given to compositions in which component (A) is a thermoplastic polymer comprising nitrogen, oxygen and/or sulphur, especially nitrogen or oxygen, in the main chain.

Also of interest are compositions in which component (A) is a polyolefin, for example polyethylene or polypropylene.

Incorporation into the organic polymers, for example into the synthetic organic and, in particular, thermoplastic polymers, can be carried out by addition of the novel biphenyl-substituted triazine compound and any further additives by the methods conventional in the art. The incorporation can expedient1y be made before or during shaping, for example by mixing the pulverulent components or by adding the stabilizer to the melt or solution of the polymer, or by applying the dissolved or dispersed compounds to the polymer, with or without subsequent evaporation of the solvent. Elastomers can also be stabilized as latices. Another way of incorporating the novel mixtures into polymers comprises adding them before or during polymerization of the corresponding monomers or before crosslinking.

The novel mixtures can also be added to the plastics to be stabilized in the form of a master batch which comprises these compounds, for example, in a concentration of from 2.5 to 25% by weight.

The novel mixtures can expediently be incorporated by the following methods:

- as an emulsion or dispersion (for example to latices or emulsion polymers)
- as a dry mix during mixing of additional components or polymer mixtures
- by direct addition to the processing equipment (for example extruders, internal mixers, etc.)
- as a solution or melt.

The stabilized polymer compositions obtained in this way can be converted into shaped articles, for example fibers, films, tapes, sheets, sandwich boards, containers, pipes and other profiles, by conventional methods, for example hot pressing, spinning, extrusion or injection moulding.

The invention therefore additionally relates to the use of the polymer composition according to the invention for the production of a shaped article.

Use in multilayer systems is also of interest. In this case, a novel polymer composition having a relatively high content of novel stabilizer, for example, 5–15% by weight, is applied in a thin film (10–100 $\mu$m) to a shaped article made from a polymer containing little or no stabilizer of the formula (1) or (1a). Application may be made at the same time as the shaping of the base structure, for example by coextrusion. However, application can also be made to the ready-formed base structure, for example by lamination with a film or by coating with a solution. The outer layer or layers of the finished article have the function of a UV filter, which protects the interior of the article from UV light. The outer layer preferably contains 5–15% by weight, in particular 5–10% by weight, of at least one compound of the formula (1) or (1a).

The polymers stabilized in this way are notable for high weathering resistance, especially for high resistance to UV light. This enables them to retain their mechanical properties and their colour and gloss for a long time even when used outside.

Likewise of particular interest is the use of the novel mixtures comprising compounds of the formula (1) or (1a) as stabilizers for coatings, for example for paints. The invention therefore also relates to those compositions whose component (A) is a film-forming binder for coatings.

The novel coating composition preferably comprises 0.01–10 parts by weight of (B), in particular 0.05–10 parts by weight of (B), especially 0.1–5 parts by weight of (B), per 100 parts by weight of solid binder (A).

Multilayer systems are possible here as well, where the concentration of the novel stabilizer (component (B)) in the outer layer can be relatively high, for example from 1 to 15 parts by weight of (B), in particular 3–10 parts by weight of (B), per 100 parts by weight of solid binder (A).

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates.

The binder (component (A)) can in principle be any binder which is customary in industry, for example those described in Ullmann's Encyclopedia of Industrial Chemistry, 5th Edition, Vol. A18, pp. 368–426, VCH, Weinheim 1991. In general, it is a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component (A) can be a cold-curable or hot-curable binder; the addition of a curing catalyst may be advantageous. Suitable catalysts which accelerate curing of the binder are described, for example, in Ullmann's Encyclopedia of Industrial Chemistry, Vol. A18, p.469, VCH Verlags-gesellschaft, Weinheim 1991.

Preference is given to coating compositions in which component (A) is a binder comprising a functional acrylate resin and a crosslinking agent.

Examples of coating compositions containing specific binders are:

1. paints based on cold- or hot-crosslinkable alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. one-component polyurethane paints based on blocked isocyanates, isocyanurates or polyisocyanates which are deblocked during baking;
4. two-component paints based on (poly)ketimines and aliphatic or aromatic isocyanates, isocyanurates or polyisocyanates;
5. two-component paints based on (poly)ketimines and an unsaturated acrylate resin or a polyacetoacetate resin or a methacrylamidoglycolate methyl ester;
6. two-component paints based on carboxyl- or amino-containing polyacrylates and polyepoxides;
7. two-component paints based on acrylate resins containing anhydride groups and on a polyhydroxy or polyamino component;
8. two-component paints based on (poly)oxazolines and acrylate resins containing anhydride groups, or unsaturated acrylate resins, or aliphatic or aromatic isocyanates, isocyanurates or polyisocyanates;
9. two-component paints based on unsaturated polyacrylates and polymalonates;
10. thermoplastic polyacrylate paints based on thermoplastic acrylate resins or externally crosslinking acrylate resins in combination with etherified melamine resins;
11. paint systems based on siloxane-modified or fluorine-modified acrylate resins.

In addition to components (A) and (B), the coating composition according to the invention preferably comprises as component (C) a light stabilizer of the sterically hindered amine and/or 2-hydroxyphenyl-2H-benzotriazole type, for example as mentioned in the above list in sections 2.1 and 2.6. To achieve maximum light stability, it is of particular interest to add sterically hindered amines as set out in the abovementioned list under 2.6. The invention therefore also relates to a coating composition which in addition to components (A) and (B) comprises as component (C) a light stabilizer of the sterically hindered amine type.

This stabilizer is preferably a 2,2,6,6-tetraalkylpiperidine derivative containing at least one group of the formula

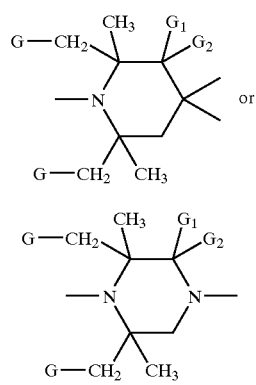

in which G is hydrogen or methyl, especially hydrogen, and $G_1$ and $G_2$ are H or together are =O.

Component (C) is preferably used in an amount of 0.05–5 parts by weight per 100 parts by weight of the solid binder.

Examples of tetraalkylpiperidine derivatives which can be used as component (C) are given in EP-A-356 677, pages 3–17, sections a) to f). These sections of this EP-A are regarded as part of the present description. It is particular expedient to employ the following tetraalkylpiperidine derivatives:

bis(2,2,6,6-tetramethylpiperid-4-yl)succinate,
bis(2,2,6,6-tetramethylpiperid-4-yl)sebacate,
bis(1,2,2,6,6-pentamethylpiperid-4-yl)sebacate,
di(1,2,2,6,6-pentamethylpiperid-4-yl)butyl-(3,5-di-tert-butyl-4-hydroxybenzyl)malonate,
bis(1-octyloxy-2,2,6,6-tetramethylpiperid-4-yl)sebacate,
tetra(2,2,6,6-tetramethylpiperid-4-yl)butane-1,2,3,4-tetracarboxylate,
tetra(1,2,2,6,6-pentamethylpiperid-4-yl)butane-1,2,3,4-tetracarboxylate,
2,2,4,4-tetramethyl-7-oxa-3,20-diaza-21-oxo-dispiro [5.1.11.2]heneicosane,
8-acetyl-3-dodecyl-1,3,8-triaza-7,7,9,9-tetramethylspiro [4.5]decane-2,4-dione,
or a compound of the formulae

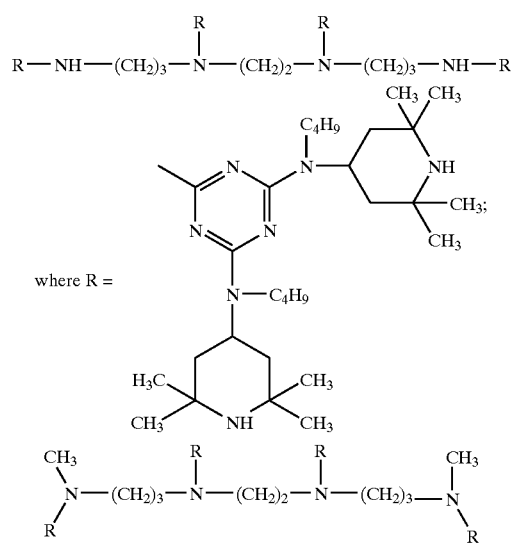

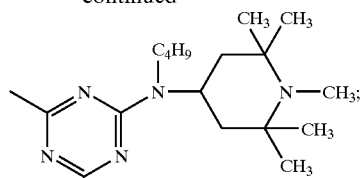

where R =

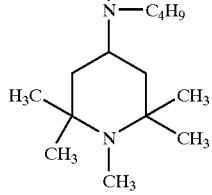

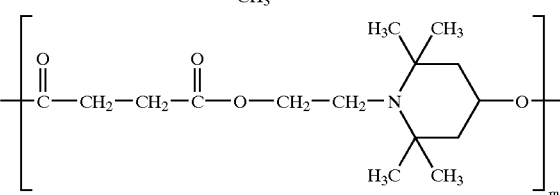

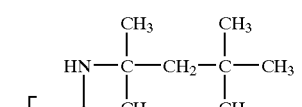

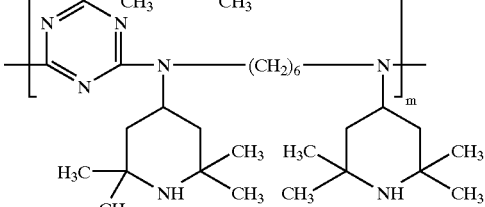

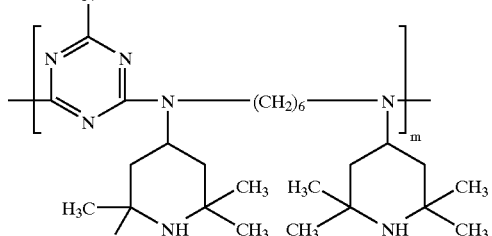

oder

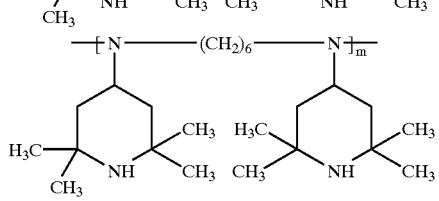

in which m is 5–50.

Apart from components (A), (B) and, if used, (C), the coating composition can also comprise further components, examples being solvents, pigments, dyes, plasticizers, stabilizers, thixotropic agents, drying catalysts and/or levelling agents. Examples of possible components are those described in Ullmann's Encyclopedia of Industrial Chemistry, 5th Edition, Vol. A18, pp. 429–471, VCH, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr, or organometallic compounds such as organotin compounds, for example.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate, and the alkoxides of these metals.

Examples of organotin compounds are dibutyltin oxide, dibutyltin dilaurate or dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride. Amino-containing resins are simultaneously binder and curing catalyst. Examples thereof are amino-containing acrylate copolymers.

The curing catalyst used can also be a phosphine, for example triphenylphosphine.

The novel coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the above-mentioned publication Ullmann's Encyclopedia of Industrial Chemistry, 5th Edition, Vol. A18, pages 451–453. In radiation-curable coating compositions, the novel stabilizers can also be employed without the addition of sterically hindered amines.

The coating compositions according to the invention can be applied to any desired substrates, for example to metal, wood, plastic or ceramic materials. They are preferably used as topcoat in the finishing of automobiles. If the topcoat comprises two layers, of which the lower layer is pigmented and the upper layer is not pigmented, the novel coating composition can be used for either the upper or the lower layer or for both layers, but preferably for the upper layer.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491–500.

Depending on the binder system, the coatings can be cured at room temperature or by heating. The coatings are preferably cured at 50–150° C., and in the case of powder coatings even at higher temperatures.

The coatings obtained in accordance with the invention have excellent resistance to the damaging effects of light, oxygen and heat; particular mention should be made of the good light stability and weathering resistance of the coatings thus obtained, for example paints.

The invention therefore also relates to a coating, in particular a paint, which has been stabilized against the damaging effects of light, oxygen and heat by a content of the compound of the formula (1) or (1a) according to the invention. The paint is preferably a topcoat for automobiles.

The invention furthermore relates to a process for stabilizing a coating based on organic polymers against damage by light, oxygen and/or heat, which comprises mixing with the coating composition a mixture comprising a compound of the formula (1) or (1a), and to the use of mixtures comprising a compound of the formula (1) or (1a) in coating compositions as stabilizers against damage by light, oxygen and/or heat.

The coating compositions can comprise an organic solvent or solvent mixture in which the binder is soluble. The coating composition can otherwise be an aqueous solution or dispersion.

The vehicle can also be a mixture of organic solvent and water. The coating composition may be a high-solids paint or can be solvent-free (e.g. a powder coating material).

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

Preference is also given to the use of the novel compound of the formula (1) or (1a) in photographic materials as stabilizer against damage by light, especially by UV light. The invention therefore also relates to a photographic material comprising a compound of the formula (1) or (1a).

The compounds according to the invention can be used for photosensitive materials of all kinds. For example, they can be employed for colour paper, colour reversal paper, direct-positive colour material, colour negative film, colour positive film, colour reversal film and other materials. They are preferably used, inter alia, for photosensitive colour material which comprises a reversal substrate or which forms positives.

Furthermore, the novel compounds can be combined with other UV absorbers, especially those which are dispersible in aqueous gelatin, for example with hydroxyphenylbenzotriazoles (cf. for example U.S. Pat. No. 4,853,471, U.S. Pat. No. 4,973,702, U.S. Pat. No. 4,921,966 and U.S. Pat. No. 4,973,701), benzophenones, oxanilides, cyanoacrylates, salicylates, acrylonitriles or thiazolines. In this context it is advantageous to employ these further, oil-dissolved UV absorbers in the photographic material in layers other than those comprising the novel UV absorbers.

In particular, it is possible successfully to stabilize photographic materials similar to those described in U.S. Pat. No. 4,518,686.

The invention therefore additionally relates to a photographic material comprising, on support, a blue-sensitive, a green-sensitive and/or a red-sensitive silver-halide emulsion layer and, if desired, a protective layer, with a layer comprising a UV absorber being arranged above the uppermost silver-halide emulsion layer, wherein the UV absorber is a compound of the formula (1) or (1a).

Preference is additionally given to photographic materials which have a layer comprising a compound of the formula (1) or (1a) above the uppermost silver-halide emulsion layer and/or between the green- and red-sensitive silver-halide emulsion layers.

Furthermore, it may be advantageous for all or some of the said layers which can comprise a UV absorber to have a UV absorber mixture and/or a further UV absorber which is dispersible in aqueous gelatin, but a compound of the formula (1) or (1a) must be present at least in one layer.

The novel material preferably has gelatin interlayers between the silver-halide emulsion layers.

Preference is given to photographic materials in which the silver halide in the blue-sensitive, green-sensitive and/or red-sensitive layer is silver chloride bromide comprising at least 90 mol % of silver chloride.

The compounds of the formula (1) or (1a) which are used in accordance with the invention can be incorporated, alone or together with the colour coupler and, if used, further additives, into the colour photographic material by dissolving the compounds beforehand in high-boiling organic solvents. It is preferred to use solvents which boil at higher than 160° C. Typical examples of such solvents are the esters of phthalic acid, phosphoric acid, citric acid, benzoic acid or of fatty acids, and also alkylamides and phenols.

Preferred colour couplers for use in the compositions of the invention, examples of such compounds, further additives such as colour cast inhibitors, DIR couplers and further light stabilizers, such as UV absorbers, phenols, phosphorus (III) compounds, organometallic complexes, hydroquinones and hydroquinone ethers, and more precise details on the structure of various photographic materials, can be found, for example, in the publications EP-A-531 258 and EP-A-520 938, and in the literature cited therein.

The novel biphenyl-substituted triazine compounds of the formula (1) or (1a) are suitable for the photochemical stabilization of undyed, dyed or printed fiber materials comprising, for example, silk, leather, wool, polyamide or polyurethanes, and especially cellulose-containing fiber materials of all kinds. Examples of such fiber materials are the natural cellulose fibers, like cotton, linen, jute and hemp, and also viscose staple fiber and regenerated cellulose.

Preferred textile fiber materials are those of cotton. The novel biphenyl-substituted triazine compounds are also suitable for the photochemical stabilization of hydroxyl-containing fibers in blend fabrics, for example blends of cotton with polyester fibers or polyamide fibers. A further preferred area of application relates to the blocking or reduction of the UV radiation which passes through the above-mentioned textile materials (UV cutting) and the heightened sun protection which textile materials finished with a novel compound offer to the human skin.

To this end, one or a number of different compounds of the formulae (1) to (4) and (1a) to (4a) are applied to the textile fiber material by one of the customary dyeing methods, advantageously in a quantity of 0.01 to 5% by weight, preferably 0.1–3% by weight and, in particular, from 0.25 to 2% by weight, based on the weight of the fiber material.

The novel biphenyl-substituted triazine compounds can be applied to the fiber material in various ways and fixed on the fiber, especially in the form of aqueous dispersions or printing pastes.

The textile fiber materials finished with the novel compounds of the formula (1) or (1a) possess improved protection against photochemical breakdown of the fiber and yellowing phenomena, and, in the case of dyed fiber material, are of enhanced (hot) light fastness. Particular emphasis should be drawn to the greatly improved photoprotective effect of the treated textile fiber material and, in particular, the good protective effect with respect to short-wave UV-B rays. This is manifested by the fact that the textile fiber material finished with a novel compound of the formula (1) or (1a) has, relative to untreated fabric, a greatly increased sun protection factor (SPF).

The sun protection factor is defined as the quotient of the dose of UV radiation which damages protected skin to that which damages unprotected skin. Accordingly, a sun protection factor is also a measure of the extent to which untreated fiber materials and fiber materials treated with a novel compound of the formula (1) or (1a) are permeable to UV radiation. The determination of the sun protection factor of textile fiber materials is explained, for example, in WO 94/04515 or in J. Soc. Cosmet. Chem. 40, 127–133 (1989) and can be carried out analogously thereto.

The UV absorbers according to the invention are suitable, furthermore, as photoprotective agents in cosmetic preparations.

The invention additionally relates, therefore, to a cosmetic preparation comprising at least one compound of the formulae (1) and (1a) and cosmetically acceptable carriers or auxiliaries.

The novel cosmetic composition contains from 0.1 to 15% by weight, preferably from 0.5 to 10% by weight, based on the overall weight of the composition, of a UV absorber of the formula (1) or (1a) and a cosmetically acceptable auxiliary.

The cosmetic composition can be prepared by physically mixing the novel UV absorber with the auxiliary by means of customary methods, for example by simply stirring together the two materials.

The cosmetic preparation according to the invention can be formulated as a water-in-oil or oil-in-water emulsion, as an oil-in-oil alcohol lotion, as a vesicular dispersion of an ionic or nonionic amphiphilic lipid, as a gel, solid stick or as an aerosol formulation.

As a water-in-oil or oil-in-water emulsion, the cosmetically acceptable auxiliary preferably contains from 5 to 50% of an oily phase, from 5 to 20% of an emulsifier and from 30 to 90% water. The oil phase mentioned can comprise any oil which is suitable for cosmetic formulations, for example one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

For the cosmetic formulations according to the invention it is possible to use any conventionally employed emulsifier, for example one or more ethoxylated esters of naturally occurring derivatives, for example polyethoxylated esters of hydrogenated castor oil; or a silicone oil emulsifier such as silicone polyol; an unmodified or ethoxylated fatty acid soap; an ethoxylated fatty alcohol; an unmodified or ethoxylated sorbitan ester; an ethoxylated fatty acid; or an ethoxylated glyceride.

The cosmetic formulation can also comprise further components, for example emollients, emulsion stabilizers, skin moisteners, tanning accelerators, thickeners such as xanthan, moisture retention agents such as glycerol, preservatives, or fragrances and colourants.

The novel cosmetic formulations are notable for good protection of human skin against the damaging effect of sunlight while at the same time providing for reliable tanning of the skin.

The examples which follow describe the invention in more detail without representing a limitation. In the examples, parts and percentages are by weight; where an example mentions room temperature, a temperature in the range 20–25° C. is meant. These definitions apply unless stated otherwise in each case.

PREPARATION EXAMPLES OF THE NOVEL COMPOUNDS

Example 1 a) 2-(4-Biphenyl)-4H-1,3-benzoxazin-4-one 15.07 g of salicyl amide are dissolved in 30 ml of xylene (+1 ml of pyridine) at boiling, and 21.7 g of biphenyl-4- carbonyl chloride dissolved in 100 ml of xylene are added over the course of 2.5 hours at 70° C. The mixture is stirred at a bath temperature of 180° C. for about 4 houUrs and then evaporated to dryness, to leave 35.3 g of an oily residue of the compound of the formula

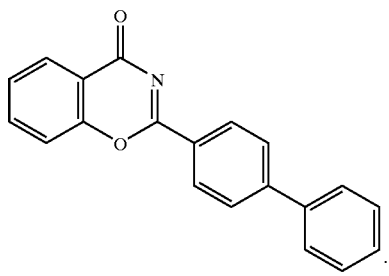

(101)

b) 2-(2-Hydroxyphenyl)-4-phenyl-6-(1-biphenyl)-1,3,5-triazine

The oily residue of the compound of the formula (101) is dissolved at 40° C. in 400 ml of methylcellosolve, and then 45.7 g of a 38% solution of benzamidine hydrochloride in methanol are added, followed by 19.6 g of a 30% sodium hydroxide solution. The mixture is subsequently stirred at 90° C. for 4 hours and filtered, to give 19.7 g of an almost colourless, crystalline product of the formula

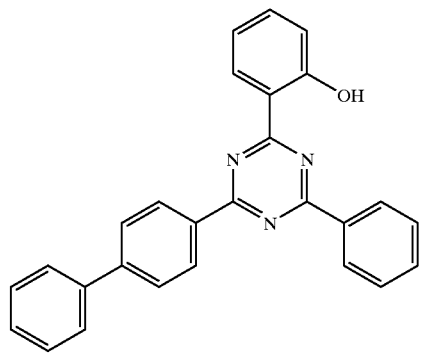

(102)

Yield: 49% of theory.
m.p.: 252–259° C.

| Elemental analysis for $C_{27}H_{19}N_3O$: | | | | |
|---|---|---|---|---|
| | C | H | N | O |
| calculated: | 80.78% | 4.77% | 10.47% | 3.99% |
| found: | 80.74% | 4.87% | 10.50% | 3.93% |

Example 2

16.15 g of 2-phenyl-4H-1,3-benzoxazin-4-one (prepared analogously to Helv. Chim. Acta 55, 1566–1599 (1972)) are dissolved in 100 ml of methanol, and 12.0 g of 4-biphenylamidine hydrochloride are added. Then 13.5 g of a 40% sodium methylate solution are added and the mixture is stirred at a bath temperature of 70° C. for 2 hours. Filtration gives 16.75 g of the compound of the formula (102).
Yield: 83.5%.

Example 3

The procedure described in Example 1b) is repeated but using 24.4 g of the compound of the formula (101) and 17 g of 4-biphenylamidine hydrochloride instead of benzamidine hydrochloride. Working up gives 21.6 g of the compound of the formula

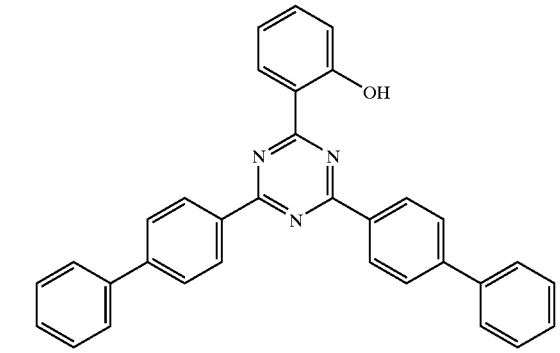

(103)

Yield: 61.5% of theory.

m.p.: 262–265° C.

| Elemental analysis for $C_{33}H_{23}N_3O \times 0.5\ H_2O$: | | | |
|---|---|---|---|
| | C | H | N |
| calculated: | 81.46% | 4.98% | 8.63% |
| found: | 81.35% | 5.08% | 8.51% |

Example 4

4.65 g of biphenylamidine hydrochloride are dissolved in 8.9 ml of dimethylacetamide. Then, in succession, 3.65 ml of a 30% methanolic sodium methylate solution, 2.97 g of methyl salicylate and 10.6 ml of cyclohexane are added, the mixture is heated to a bath temperature of 90° C. over the course of 30 minutes, and it is stirred at this temperature for 20 hours. It is then cooled to 5° C. and filtered, to give 1.05 g of a pale yellowish product of the formula (103) (see Example 3).

Yield: 22% of theory.

Example 5 a) 4.65 g of 4-biphenylamidine hydrochloride are suspended in 6.7 ml of methanol. Then, in succession, 3.6 g of 30% sodium methylate solution and 1.22 g of salicylaldehyde are added. The mixture is stirred at 60–64° C. for 6 hours and filtered, to give, after washing with water and methanol, 4.4 g of a pale beige product of the formula

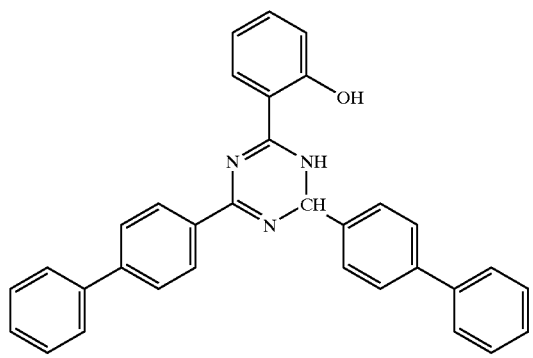

(104)

| Elemental analysis for $C_{33}H_{25}N_3O$: | | | | |
|---|---|---|---|---|
| | C | H | N | O |
| calculated: | 82.65% | 5.25% | 8.76% | 3.34 |
| found: | 81.40% | 5.19% | 8.61% | 3.85 | b) 4.8 g of the compound of the formula (104) are dissolved in 35 ml of dimethylformamide, and 3.83 ml of a 40% aqueous sodium bisulphite solution are added. The mixture is stirred at 48° C. for 6 hours. It is then filtered at room temperature and the filter product is dried, to give 4.62 g of a pale yellowish beige product of the formula (103) (see Example 3).

Yield: 96.3% of theory.

Example 6

Prior Art 4.6 g of resorcinol are dissolved in 40 ml of nitrobenzene, and then 3.82 g of 2-(4-biphenyl)-4,6-dichloro-1,3,5-triazine are added at room temperature. 3.37 g of anhydrous aluminium trichloride are then introduced, with ice cooling, so that the temperature does not rise above 20° C. The mixture is subsequently heated to a bath temperature of 92° C. and stirred at this temperature for 2 hours. It is cooled and poured into a mixture of 100 ml of $H_2O$, 90 g of ice and 10 ml of conc. HCl. Subsequent steam distillation and working up give 7.38 g of a pale yellow-orange powder of the formula

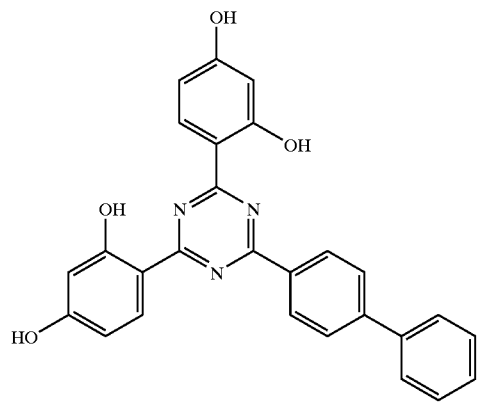

(105)

Yield: 85.2% of theory.

| Elemental analysis for $C_{27}H_{19}N_3O_4 \times 1.33\ H_2O$: | | | | |
|---|---|---|---|---|
| | C | H | N | $H_2O$ |
| calculated: | 68.5% | 4.61% | 8.88% | 5.06% |
| found: | 68.37% | 4.58% | 8.79% | 5.05% |

Example 7

2 g of the compound of the formula (105) prepared in Example 6 are dissolved in 30 ml of dimethyl methanephosphonate together with 3 g of sodium carbonate, and the solution is stirred at 150° C. for 2 hours. After cooling, it is diluted with 500 ml of ethanol and filtered to give 1.85 g of a pale beige product of the formula (106)

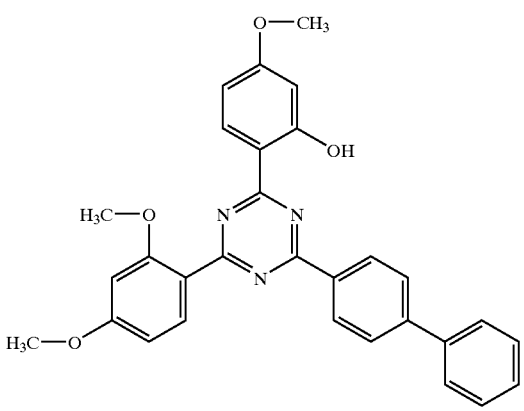

Yield: 86% of theory.

| Elemental analysis for $C_{30}H_{25}N_3O_4$: | | | |
|---|---|---|---|
| | C | H | N |
| calculated: | 73.31% | 5.13% | 8.55% |
| found: | 73.27% | 5.15% | 8.48% |

Example 8

The procedure described in Example 2 is repeated but using 2-(2-hydroxyphenyl)-4H-1,3-benzoxazin-4-one instead of 2-phenyl-4H-1,3-benzoxazin-4-one. Working up gives the compound of the formula (107)

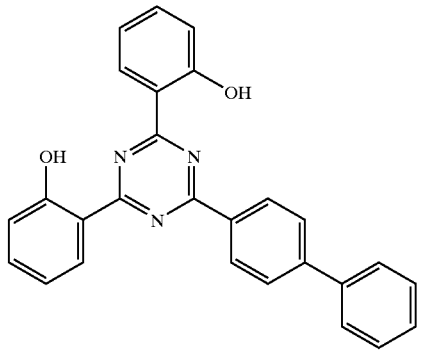

Yield: 81% of theory.

m.p.: 289–290° C.

| Elemental analysis for $C_{27}H_{19}N_3O_2$: | | | |
|---|---|---|---|
| | C | H | N |
| calculated: | 77.68% | 4.59% | 10.07% |
| found: | 77.67% | 4.64% | 10.04% |

Example 9

The procedure described in Example 7 is repeated but using the compound of the formula (107) instead of the compound of the formula (105), to give the compound of the formula (108)

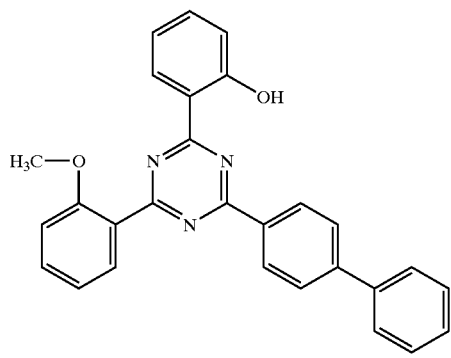

Yield: 100%.

m.p.: 228–229° C.

| Elemental analysis for $C_{28}H_{21}N_3O_2 \times 1.5\ H_2O$: | | | |
|---|---|---|---|
| | C | H | N |
| calculated: | 73.34% | 5.27% | 9.16% |
| found: | 73.4% | 4.5% | 9.1% |

Example 10

The procedure described in Example 2 is repeated but using 2-(4-methoxyphenyl)-4H-1,3-benzoxazin-4-one instead of 2-phenyl-4H-1,3-benzoxazin-4-one. Working up gives the pale beige compound of the formula (109)

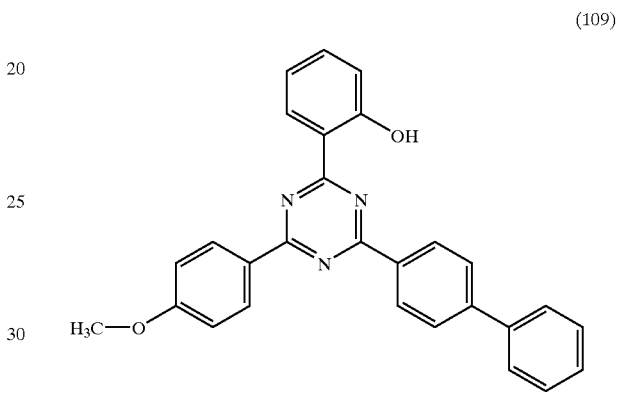

| Elemental analysis for $C_{28}H_{21}N_3O_2$: | | | |
|---|---|---|---|
| | C | H | N |
| calculated: | 77.94% | 4.91% | 9.74% |
| found: | 77.84% | 4.94% | 9.68% |

Example 11 a) The procedure described in Example 1a) is repeated, but using 4-methoxysalicylamide instead of salicylamide. The residue corresponds to the compound of the formula (110)

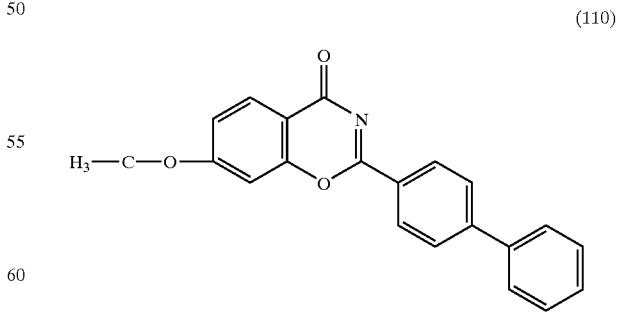

b) The compound of the formula (110) is processed further without purification as described in Example 2, using 4-biphenylamidine hydrochloride instead of benzamidine hydrochloride. This gives the compound of the formula (111)

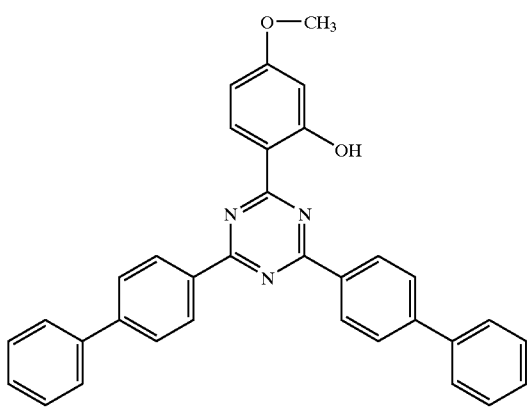

Yield: 34% of theory.

| Elemental analysis for $C_{34}H_{25}N_3O_2$: | | | |
|---|---|---|---|
| | C | H | N |
| calculated: | 80.45% | 4.96% | 8.28% |
| found: | 80.58% | 4.95% | 8.18% |

Example 12

The procedure described in Example 2 is repeated but using 2-(4-cyanophenyl)-4H-1,3-benzoxazin-4-one instead of 2-phenyl-4H-1,3-benzoxazin-4-one. Working up gives the compound of the formula (112)

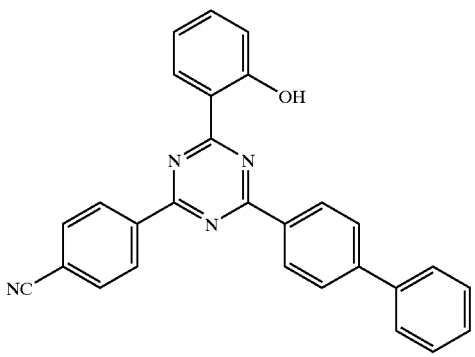

Yield: 31% of theory.

| Elemental analysis for $C_{28}H_{18}N_4O \times 0.08\ H_2O$: | | | | |
|---|---|---|---|---|
| | C | H | N | $H_2O$ |
| calculated: | 78.59% | 4.28% | 13.09% | 0.34% |
| found: | 78.57% | 4.33% | 12.91% | 0.34% |

Example 13

The procedure described in Example 2 is repeated, but using instead of 2-phenyl-4H-1,3-benzoxazin-4-one the compound of the formula (113a)

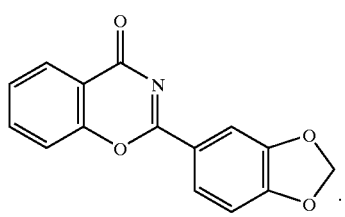

Working up gives the compound of the formula (113)

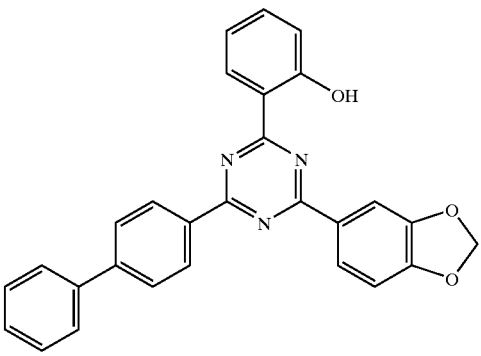

Yield: 72.6% of theory.

m.p.: 240–242° C.

| Elemental analysis for $C_{28}H_{19}N_3O_3$: | | | | |
|---|---|---|---|---|
| | C | H | N | O |
| calculated: | 75.49% | 4.3% | 9.43% | 10.77% |
| found: | 75.45% | 4.36% | 9.36% | 10.83% |

Example 14

3.6 g (0.147 mol) of magnesium are suspended in 50 ml of THF, and a solution of 34.3 g (0.147 mol) of 4-bromobiphenyl in 50 ml of THF is added dropwise. The mixture is then heated at reflux for 2 hours. This mixture is added dropwise to a solution of 9.2 g (0.05 mol) of cyanuric chloride in 50 ml of THF (50° C.). After 4 hours, 100 ml of toluene are added and the mixture is poured into 50 ml of 12% HCl, during which a product precipitates. The mixture is filtered and the filter residue is washed with water. After drying, it is chromatographed over silica gel to give 8.3 g of the product of the formula (114)

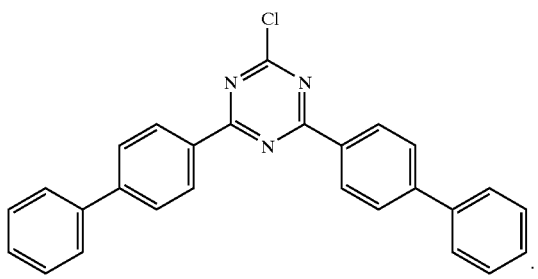

Yield: 35% of theory.

Elemental analysis for $C_{27}H_{18}N_3Cl$:

|  | C | H | N | Cl: |
|---|---|---|---|---|
| calculated: | 77.23% | 4.32% | 10.01% | 8.44% |
| found: | 77.10% | 4.52% | 9.95% | 8.13% |

Example 15

17.6 g (0.042 mol) of 2-chloro-4,6-bisbiphenyl-1,3,5-triazine (compound of the formula 114) are suspended in 100 ml of toluene. AlCl$_3$ is added as catalyst, and the mixture is heated to 100° C. 4.7 g (0.042 mol) of resorcinol are added in portions. The mixture is then heated at reflux for 12 hours. The reaction mixture is poured into an ice-water mixture, during which a product precipitates. The mixture is filtered and the filter residue is washed with water, to give 14.5 g of a product of the formula (115)

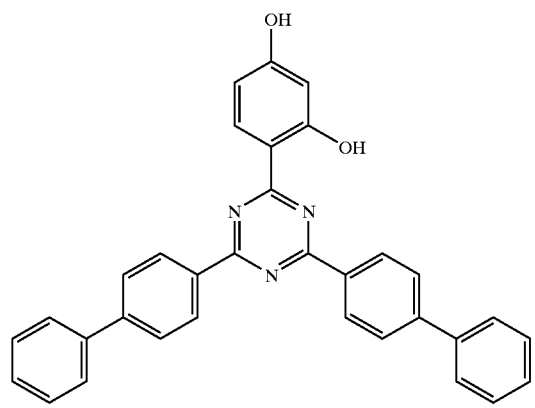

Yield: 70%.

Elemental analysis for $C_{33}H_{23}N_3O_2$:

|  | C | H | N |
|---|---|---|---|
| calculated: | 80.31% | 4.70% | 8.51% |
| found: | 80.26% | 4.55% | 8.23% |

Example 16

9.9 g (0.02 mol) of the compound of the formula (115) (see Example 15) and 3 g (0.022 mol) of potassium carbonate are suspended in 50 ml of ethylcellosolve. The mixture is heated to 110° C., and 3.6 g (0.022 mol) of 1'-bromohexane are added dropwise. The mixture is stirred at 110° C. for 21 hours. On cooling the mixture, a product is precipitated. The mixture is filtered and the filter residue is washed with water, to give a product of the formula (116)

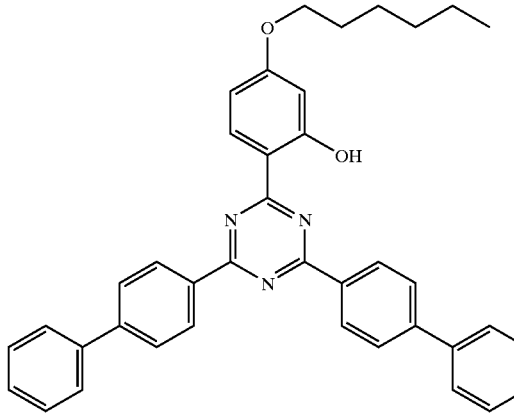

Yield: 69%.
m.p.: 176–178° C.

Elemental analysis for $C_{39}H_{35}N_3O_2$:

|  | C | H | N |
|---|---|---|---|
| calculated: | 81.08% | 6.11% | 7.27% |
| found: | 80.91% | 6.28% | 7.14% |

Example 17

8.5 g (0.0172 mol) of the compound of formula (115) (see Example 15), 3.4 g (0.025 mol) of butyl glycidyl ether and 0.5 g (0.0014 mol) of ethyltriphenylphosphonium bromide are suspended in 200 ml of xylene. The mixture is heated at reflux for 17 hours. The xylene is evaporated off and the residue is recrystallized, to give 6.5 g of the compound of the formula (117)

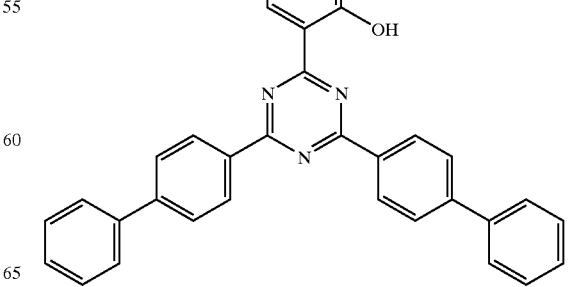

Yield: 61%.

m.p.: 156–158° C.

| Elemental analysis for $C_{40}H_{37}N_3O_4$: | | | |
|---|---|---|---|
| | C | H | N |
| calculated: | 77.02% | 5.98% | 6.74% |
| found: | 76.78% | 5.97% | 6.72% |

Example 18

23.2 g (0.047 mol) of the compound of the formula (115) (see Example 15) and 7.2 g (0.052 mol) of potassium carbonate are suspended in 100 ml of ethylcellosolve. The mixture is heated to 110° C., and 10 g (0.052 mol) of 1-bromooctane are added dropwise. The mixture is stirred at 130° C. for 3 hours. On cooling the mixture, a product is precipitated. The mixture is filtered and the filter residue is washed with water, to give 13.3 g of the compound of the formula (118)

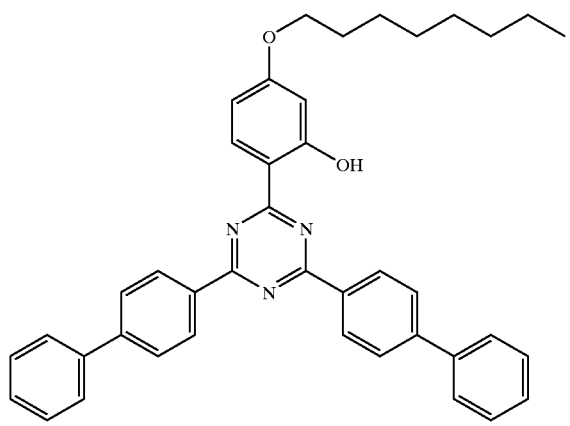

Yield: 47%.

m.p.: 158–160° C.

Example 19

8.1 g (0.0165 mol) of the compound of formula (115) (see Example 15), 6.8 g (0.028 mol) of a $C_{12}/C_{13}$-alkyl glycidyl ether isomer mixture and 0.6 g (0.0016 mol) of ethyltriphenylphosphonium bromide are suspended in 150 ml of xylene. The mixture is heated at reflux for 23 hours. The solvent is evaporated off and the residue is chromatographed over silica gel, to give 9.8 g of the compound of the formula (119)

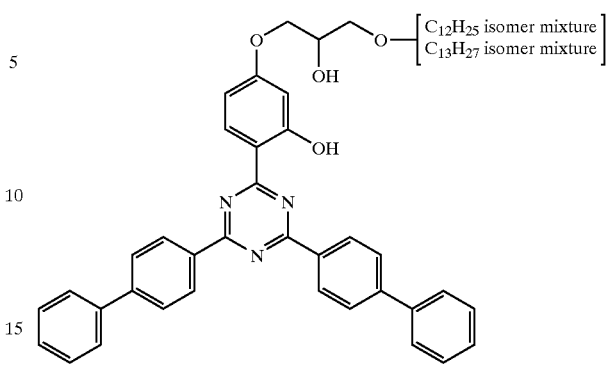

Yield: 81%.
m.p.: 80–88° C.

Example 20

22.2 g (0.045 mol) of 2-(2,4-dihydroxyphenyl)-4,6-bisbiphenyl-1,3,5-triazine, corresponding to the formula (115), and 6.8 g (0.05 mol) of potassium carbonate are suspended in 150 ml of ethylcellosolve. The mixture is heated to 110° C., and 10.9 g (0.05 mol) of 1-bromodecane are added dropwise. The mixture is stirred at 110° C. for 12 hours. On cooling the mixture, a product is precipitated. The mixture is filtered and the residue is recrystallized to give 8 g of a compound of the formula (120)

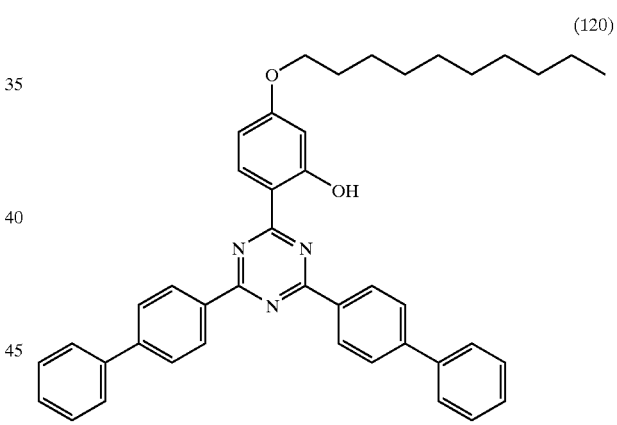

(Yield 28%, m.p.: 154–157° C.).

| Elemental analysis (%) | | | |
|---|---|---|---|
| | C | H | N |
| calculated: | 81.48 | 6.84 | 6.63 |
| found: | 81.41 | 6.74 | 6.62 |

Example 21

10 g (0.016 mol) of 2-(2-hydroxy-4-(2-hydroxy-3-butyloxypropoxy)phenyl)-4,6-bisbiphenyl-1,3,5-triazine, corresponding to the formula (117), in 100 ml of a xylene isomer mixture are heated to 120° C. Then 4.7 g (0.0352 mol) of caproyl chloride are added dropwise. 5 drops of pyridine are added as well, and the mixture is stirred at 120°

C. for 12 hours. The mixture is cooled and the organic phase is washed with water and then dried over MgSO$_4$. After evaporation of the solvent, the residue is chromatographed over silica gel to give 8.6 g of a compound of the formula (121)

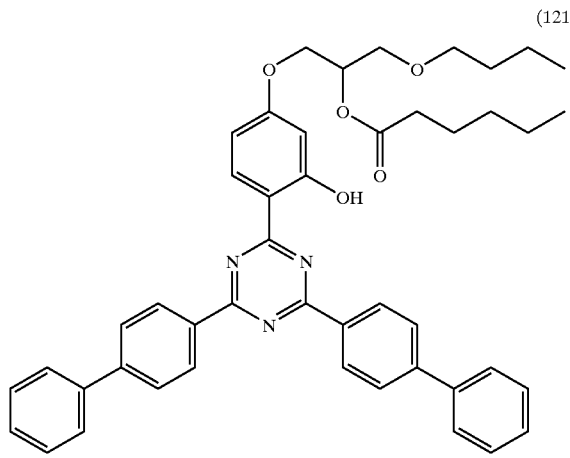

as a resin (Yield 74%).

| Elemental analysis (%) | | | |
|---|---|---|---|
| | C | H | N |
| calculated | 76.54 | 6.56 | 5.82 |
| found: | 76.27 | 6.66 | 5.30 |

Example 22

2.3 g (0.025 mol) of the compound of the formula (115) and 5.18 g (0.0375 mol) of potassium carbonate is suspended in 150 ml of ethylcellosolve, the mixture is heated to 110° C., and 9.35 g (0.0375 mol) of 1-bromododecane are added. The mixture is stirred at 110° C. for 12 hours. On cooling the mixture, a product is precipitated. The mixture is filtered and the residue is recrystallized to give 6.3 g of a compound of the formula (122)

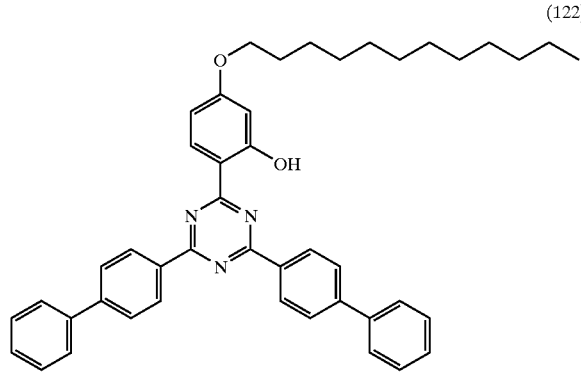

(Yield 38%, m.p.: 143–146° C.).

| Elemental analysis (%) | | | |
|---|---|---|---|
| | C | H | N |
| calculated: | 81.66 | 7.16 | 6.35 |
| found: | 81.66 | 7.33 | 6.21 |

Example 23

The benzoxazinone of the formula (101) is reacted as described in Example 1 with the following substituted benzamidines:

a. with 3-amidobenzamide of the formula

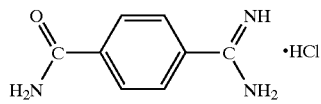

to give the compound of the formula (123a)

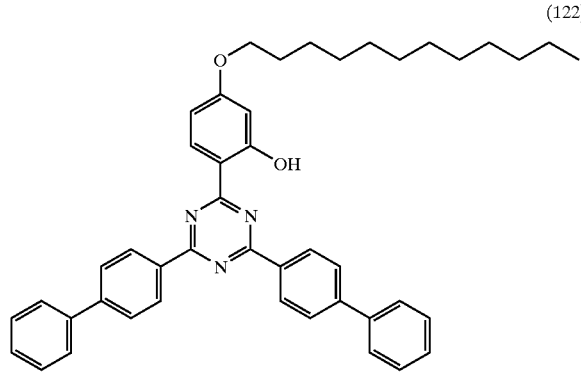

m.p.: 297–298° C.

| Elemental analysis for C$_{28}$H$_{20}$N$_4$O$_2$: | | | | |
|---|---|---|---|---|
| | C | H | N | O |
| calculated: | 75.66 | 4.54 | 12.6 | 7.2 |
| found: | 75.65 | 4.65 | 12.57 | 7.13 | b) with methyl 4-amidobenzoate of the formula

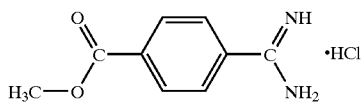

to give the compound of the formula (123b)

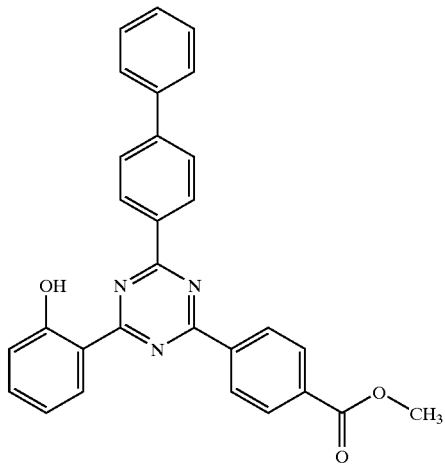

m.p.: 198–200° C.

Elemental analysis for $C_{29}H_{21}N_3O_3$:

|  | C | H | N | O |
|---|---|---|---|---|
| calculated: | 75.80 | 4.61 | 9.14 | 10.45 |
| found: | 75.81 | 4.88 | 9.02 | 10.29 |

Example 24

9.4 g (0.019 Mol) 2-(2,4-dihydroxyphenyl)-4,6-bis-(4-biphenyl)-1,3,5-triazine are suspended in 100ml of ethyl methyl ketone, 2.6 g (0.019 Mol) potassium carbonate and 6.1 g (0.021 Mol) 2-bromopentane acid octylester (octyl isomeric mixture). The mixture is stirred for 12 hours at 100° C., then filtered and reduced. The residue is chromatographed over silica gel, to give 6.3 g (47%) of a waxy product of the formula (124)

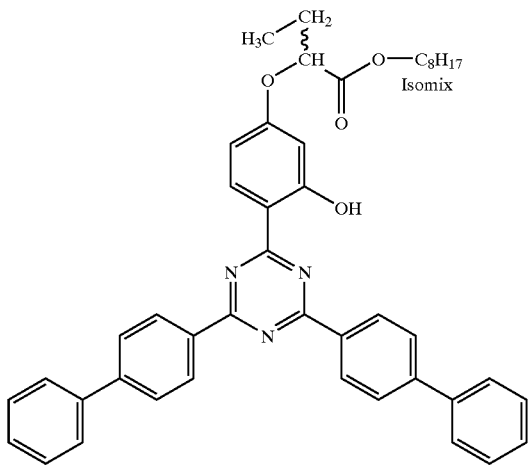

$^1$H-NMR-spectrum is in accordance with the formula.

Elemental analysis for $C_{45}H_{37}N_3O_4$:

|  | C | H | N |
|---|---|---|---|
| calculated: | 78.27 | 6.71 | 5.95 |
| found: | 79.25 | 7.18 | 5.18 |

Using 2-bromopropane acid octyl ester (octyl isomeric mixture) instead of the above bromoalkyl ester in the same procedure gives 2-(2-hydroxy-4-{1-octyloxycarbonylethyloxy}-phenyl)-4,6-bis(4-biphenylyl)-1,3,5-triazine.

USE EXAMPLES

Example 25

Stabilization of a 2-coat metallic finish

The compounds to be tested are dissolved in 20–30 g of Solvesso® 150 and tested in a clearcoat having the following composition:

| Synthacryl ® SC 303[1] | 27.51 |
|---|---|
| Synthacryl ® SC 370[2] | 23.34 |
| Maprenal ® 650[3] | 27.29 |
| Butyl acetate/Butanol (37/8) | 4.33 |
| Isobutanol | 4.87 |
| Solvesso ® 150[4] | 2.72 |
| Crystal Oil K-30 | 8.74 |
| Levelling assistant Baysilon ® MA[5] | 1.20 |
|  | 100.00 g |

[1]Acrylate resin, Hoechst AG; 65% solution in xylene/butanol 26:9
[2]Acrylate resin, Hoechst AG; 75% solution in Solvesso ® 100
[3]Melamine resin, Hoechst AG; 55% solution in isobutanol
[4]aromatic hydrocarbon mixture, boiling range 182–203° C. (Solvesso ® 150) or 161–178° C. (Solvesso ® 100); manufacturer: Esso
[5]1% in Solvesso ® 150; manufacturer: Bayer AG 1.5% of the compounds to be tested are added to the clearcoat, based on the solids content of the varnish. Some further varnish samples are prepared which, in addition to the novel compounds, contain 1% of the compound of the formula (125)

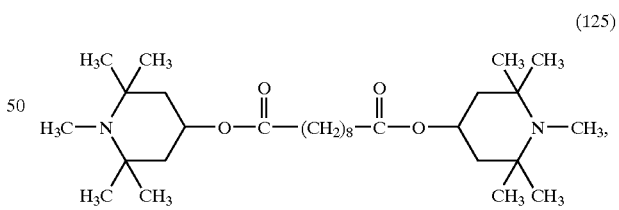

based on the solids content of the coating composition. For comparison, a clearcoat containing no light stabilizer is used.

The clearcoat is diluted with Solvesso® 100 to spray viscosity and is applied by spraying to a prepared aluminium panel (Uniprime Epoxy, silver-metallic basecoat) which is baked at 130° C., for 30 minutes, to give a dry film thickness of 40–50 μm of clearcoat.

The samples are subjected to weathering as follows:

UVCON® weathering instrument from Atlas Corporation (UVB-313 lamps) with a cycle of 8 h radiation at 70° C. and 4 h condensation at 50° C.

QUV® weathering instrument from Q-Panel (UVA-340 lamps—high intensity) with a cycle of 8 h radiation at 70° C. and 4 h condensation at 50° C.

The surface gloss (20° gloss, DIN 67530) of the samples is measured.

Compounds Used:
Compound of the formula (116) (Example 16)
Compound of the formula (119) (Example 19)
Compound of the formula (121) (Example 21)
Results:

TABLE 1

20° gloss after 0, 1200 h weathering in the UVCON (UVB-313) bisbiphenyltriazines alone

|  | 0 | 1200 |
|---|---|---|
| unstabilized | 87 | 70 |
| compound of the formula (116) | 88 | 84 |
| 1.5% of the compound of the formula (119) | 85 | 87 |
| 1.5% of the compound of the formula (121) | 87 | 86 |

TABLE 2

20° gloss after 0, 1200 h weathering in the UVCON (UVB-313); combination of bisbiphenyltriazines with Tinuvin 292 (HALS)

|  | 0 | 1200 |
|---|---|---|
| unstabilized | 87 | 70 |
| 1% of the compound of the formula (125) | 87 | 76 |
| 1.5% of the compound of the formula (116)/ 1% of the compound of the formula (125) | 87 | 82 |
| 1.5% of the compound of the formula (119)/ 1% of the compound of the formula (125) | 87 | 84 |
| 1.5% of the compound of the formula (121)/ 1% of the compound of the formula (125) | 87 | 86 |

TABLE 3

20° gloss after 0, 1200 h weathering in the QUV-A (high intensity) bisbiphenyltriazines alone

|  | 0 | 1200 |
|---|---|---|
| unstabilized | 87 | 60 |
| 1.5% of the compound of the formula (116) | 88 | 89 |
| 1.5% of the compound of the formula (119) | 85 | 88 |
| 1.5% of the compound of the formula (121) | 87 | 90 |

TABLE 4

20° gloss after 0, 1200 h weathering in the QUV-A (high intensity) Combination of bisbiphenyltriazines with Tinuvin 292 (HALS)

|  | 0 | 1200 |
|---|---|---|
| unstabilized | 87 | 60 |
| 1% of the compound of the formula (125) | 87 | 84 |
| 1.5% of the compound of the formula (116)/ 1% of the compound of the formula (125) | 87 | 90 |
| 1.5% of the compound of the formula (119)/ 1% of the compound of the formula (125) | 87 | 90 |
| 1.5% of the compound of the formula (121)/ 1% of the compound of the formula (125) | 87 | 90 |

The results listed in Tables 1 to 4 show that the samples stabilized in accordance with the invention have better weathering stability (gloss retention) than the unstabilized comparison sample.

Example 26

Use in Polycarbonate 10 g of polycarbonate powder (Lexan 115) are dissolved with stirring in 50 g of methylene chloride at room temperature, a process which takes several hours. Also added is 0.2 g of UV absorber, corresponding to a 2% concentration of additive. These solutions are used to cast films with a thickness of 20 μm.

The films are exposed in an Atlas Weatherometer CI 65 at a black panel temperature of 63° C. and a relative humidity of 60%. The discolouration of the samples is checked at regular intervals by measuring the Yellowness Index (YI, method DIN 6167). Table 5 shows the exposure time until a Yellowness Index of 7 is obtained.

The films are then exposed further until they become brittle, which is shown by the development of cracks in the films. The duration of exposure until embrittlement occurs is likewise given in Table 5.

TABLE 5

Exposure time (h) until Yellowness Index (YI) of 7 is reached and until embrittlement.

|  | Exposure time (h) until | |
|---|---|---|
| UV absorber | YI = 7 | Embrittlement |
| none | 990 | 1000 |
| 2% of the compound of the formula (126) | 1320 | 4057 |
| 2% of the compound of the formula (102) | 2480 | 6060 |

The following UV absorbers are employed:
a) compound of the formula

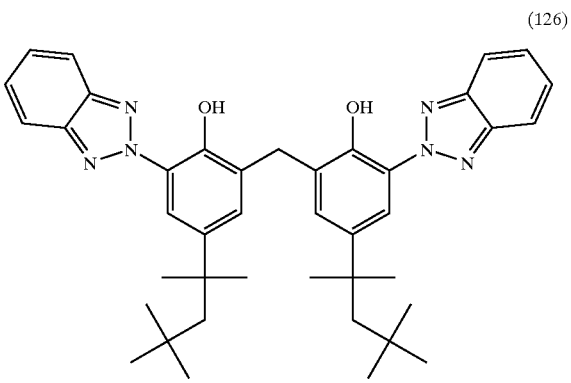

(126)

b) compound of the formula (102) from Example 1b)

Example 27

Polycarbonate powder is mixed with 0.3% of the UV absorber of the formula (102) and the mixture is processed to give granules in a twin-screw extruder at a melt temperature of 275° C. at a speed of 25 rpm.

The granules are injection-moulded (240/300° C./75 bar) to give sheets measuring 67×43×2 mm. The sheets are exposed in an Atlas Weatherometer CI 65, as described in Example 25. Table 6 shows the exposure time until a Yellowness Index of 20 is obtained (YI, measured in accordance with DIN 6167).

TABLE 6

| | Exposure time (h) until a Yellowness Index (YI) of 10; 15; 20; is reached | | |
|---|---|---|---|
| | Exposure time (h) until YI = | | |
| UV absorber | 10 | 15 | 20 |
| none | 375 | 695 | 940 |
| compound of the formula (102) | 1160 | 1600 | 3950 |

Example 28

10 g of polycarbonate powder (Lexan 115) are dissolved with stirring in 50 g of methylene chloride at room temperature, a process which takes several hours. Also added is 0.2 g of the UV absorber of formula (116), corresponding to a 2% concentration of additive. These solutions are used to cast films with a thickness of 20 μm.

The films are exposed in an Atlas Weatherometer CI 65 at a black panel temperature of 63° C. and a relative humidity of 60%. The discolouration of the samples is checked at regular intervals by measuring the Yellowness Index (YI, method DIN 6167). Table 7 gives the difference in the Yellowness Index (ΔYI) between the value after 500 and 1000 hours and the initial value.

TABLE 7

| | ΔYI after exposure | |
|---|---|---|
| UV absorber | 500 h | 1000 h |
| none | 2.2 | 7.1 |
| 2% of the compound of the formula (116) | 0.5 | 1.1 |

Example 28

Cosmetic Use

| Suspension of the compound of formula (120) | |
|---|---|
| Biphenyl-triazin-UV-absorber of the formula (120) | 3 g |
| $C_8$—$C_{12}$-fatty alcohol polyglucoside | 2.4 g |
| sodium chloride | 1 g |
| Xanthan gum | 0.5 g |
| Bronopol | 0.1 g |
| deionized water | 93 g |

Preparation of the Formulation 40 g of the UV absorber, 20 g of the fatty alcohol polyglucoside and 40 g water are mixed together und milled with a ball mill (Drais), so that the diameter of the milled particles becomes smaller than 1 μm. Starting form this paste the other components of the above dispensing are admixed accordingly.

The measured sun protection factors (SPF) and photo stabilities can be seen from Table 8.

TABLE 10

| | concentration | sun protection factor*) | photo stability**) [h] |
|---|---|---|---|
| compound of the formula (120) | 3% | 19.7 | 1400 h |

*)by Diffey und Robson
**)as half-life period of the photochemical decomposition in D65-light in ethanolic solution.

The results show that the effective substances have a high photo stability and that a high sun protection factor can be obtained with a low concentration.

What is claimed is:

1. A composition comprising (A) an organic material which is sensitive to damage by light, oxygen and/or heat, and (B) as stabilizer, a compound of formula (1) or (1a)

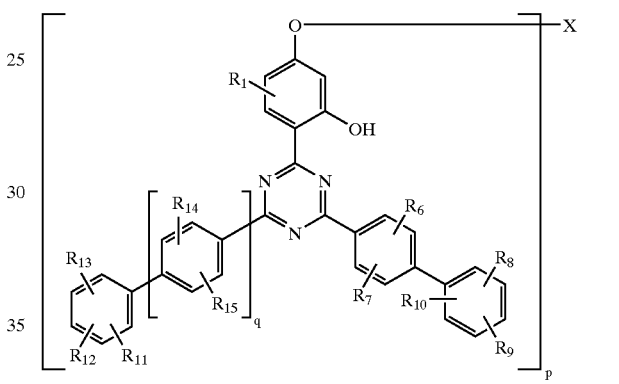

(1)

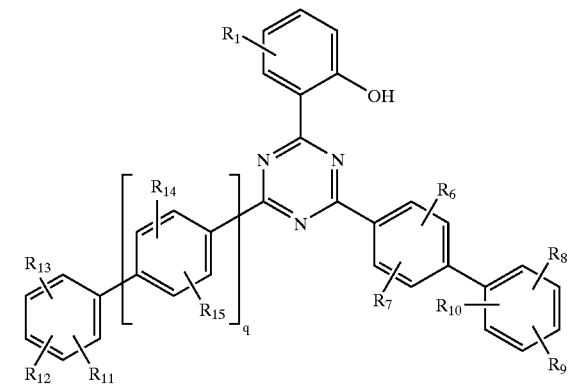

(1a)

where $R_1$ is hydrogen; $C_1$–$C_{24}$alkyl or $C_5$–$C_{12}$cycloalkyl; or $R_1$ is $C_1$–$C_{24}$alkyl or $C_5$–$C_{12}$cycloalkyl, each of which is substituted by halogen, —$R_4$, —$OR_5$, —$N((R_5)_2$, =$NR_5$, =O, —$CON(R_5)_2$, —$COR_5$, —$COOR_5$, —$OCOR_5$, —$OCON(R_5)_2$; —CN, —$NO_2$, —$SR_5$, —$SOR_5$, —$SO_2R_5$, —$P(O)(OR_5)_2$, a morpholinyl, piperidyl, 2,2,6,6-tetramethylpiperidyl, piperazinyl or N-methylpiperazinyl-group, or combinations thereof; and/or $R_1$ is $C_1$–$C_{24}$alkyl or $C_5$–$C_{12}$cycloalkyl which is interrupted by 1 to 6 phenylene, —O—, —$NR_5$—, —$CONR_5$—, —COO—, —OCO—, —$CH(R_5)$—, —C(R$_5$)$_2$— or —CO— groups or combinations thereof; C$_2$–C$_{24}$alkenyl; halogen; —SR$_3$, SOR$_3$; SO$_2$R$_3$; —SO$_3$H; —SO$_3$M; or a radical of the formula

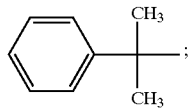

R$_3$ is C$_1$–C$_{20}$alkyl; C$_3$–C$_{18}$alkenyl; C$_5$–C$_{12}$cycloalkyl; C$_7$–C$_{15}$phenylalkyl, or C$_6$–C$_{12}$aryl which is unsubstituted or substituted by 1 to 3 C$_1$–C$_4$alkyl groups;

R$_4$ C$_6$–C$_{12}$aryl; or C$_6$–C$_{12}$aryl which is substituted by halogen, C$_1$–C$_8$alkyl, C$_1$–C$_8$alkoxy or combinations thereof; C$_5$–C$_{12}$cycloalkyl; C$_7$–C$_{15}$phenylalkyl; or C$_7$–C$_{15}$phenylalkyl which is substituted in the phenyl ring by 1 to 3 halogen atoms, C$_1$–C$_8$alkyl, C$_1$–C$_8$alkoxy or combinations thereof or C$_2$–C$_8$alkenyl;

R$_5$ is R$_4$; hydrogen; C$_1$–C$_{24}$alkyl; or a radical of the formula

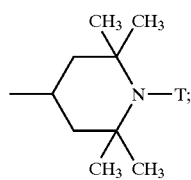

(1a)

T is hydrogen; C$_1$–C$_8$alkyl; C$_2$–C$_8$alkyl which is substituted by hydroxyl or acyloxy groups; oxyl; hydroxyl; —CH$_2$CN; C$_1$–C$_{18}$alkoxy; C$_5$–C$_{12}$cycloalkoxy; C$_3$–C$_6$alkenyl; C$_7$–C$_9$phenylalkyl; C$_7$–C$_9$phenylalkyl which is substituted one, two or three times in the phenyl ring by C$_1$–C$_4$alkyl; or aliphatic C$_1$–C$_8$alkanoyl;

R$_6$ to R$_{15}$ independently of one another are hydrogen; hydroxyl; —C≡N; C$_1$–C$_{20}$alkyl; C$_1$–C$_{20}$alkoxy; phenyl-C$_1$–C$_{20}$alkoxy; C$_7$–C$_{20}$phenylalkyl; C$_4$–C$_{12}$cycloalkyl; C$_4$–C$_{12}$cycloalkoxy; halogen; halo-C$_1$–C$_5$alkyl; carboxyl; acylamino; acyloxy; C$_1$–C$_{12}$alkoxycarbonyl; aminocarbonyl; —O—Y; or O-Z; or R$_{11}$ and R$_{12}$, together with the phenyl radical, form a cyclic radical containing 2 to 4 carbon atoms which is interrupted by oxygen or —NR$_5$—.

M is alkali metal;

p 1 or 2;

q 0 or 1;

if p is 1,

X, Y and Z independently of one another are hydrogen; C$_3$–C$_{50}$alkyl which is interrupted by oxygen and/or substituted by R$_2$ or OR$_2$; ((CH$_2$)$_m$—CH$_2$—O—)$_n$—R$_2$; —(CH$_2$—CH((CH$_2$)$_{m-R2}$)—O—)$_{n-R'2}$; —(CH ((CH$_2$)$_m$—R$_2$)—CH$_2$—O—)$_n$—R'$_2$; —(CH$_2$)$_n$—R$_2$;

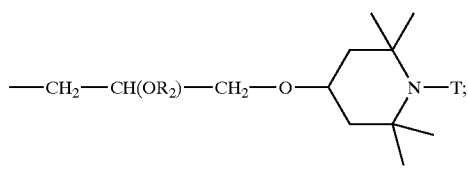

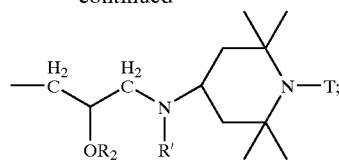

C$_4$–C$_{12}$cycloalkyl which is substituted by R$_2$; —OR$_2$-substituted C$_4$–C$_{12}$cycloalkyl; —CH((CH$_2$)$_n$—R$_2$)—CO—O—(CH$_2$)$_m$—R'$_2$; —CH((CH$_2$)$_n$—R$_2$)—CO—(NR')—(CH$_2$)$_m$—R'$_2$; —CO—(CH$_2$)$_n$—R$_2$; —CO—O—(CH$_2$)$_n$—R$_2$, —CH$_2$—CH(—O(CO)—R$_2$)—R'$_2$; —CO—NR'—(CH$_2$)$_n$—R$_2$; C$_6$–C$_{12}$aryl; allyl; C$_4$–C$_{20}$alkenyl which is interrupted by oxygen; C$_4$–C$_{12}$cycloalkenyl; C$_4$–C$_{12}$cycloalkynyl; which is interrupted by oxygen; or C$_3$–C$_{20}$alkynyl;

R$_2$ and R'$_2$, independently of one another are R$_x$ if attached to a carbon atom and are R$_y$ if attached to an atom other than carbon;

n 0 to 20;

m 0 to 20;

and, if p is 2,

Y and Z, independently of one another are as defined for when p is 1; and

X is C$_2$–C$_{12}$alkylene; —CO—(C$_2$–C$_{12}$alkylene)—CO—; —CO-phenylene-CO—; CO-biphenylene-CO—; CO—O—(C$_2$–C$_{12}$alkylene)—O—CO—; —CO—O-phenylene-O—CO—; —CO—O-biphenylene-O—CO—; —CO—NR'—(C$_2$–C$_{12}$alkylene)—NR'—CO—; —CO—NR'-phenylene-NR'—CO—; —CO—NR'-biphenylene-NR'—CO—; —CH$_2$—CH(OH)—CH$_2$—; —CH$_2$—CH(OR$_2$)—CH$_2$—; —CH$_2$—CH(OH)—CH$_2$—O-D-O—CH$_2$—CH(OH)—CH$_2$; —CH$_2$—CH(OR$_2$)—CH$_2$—O-D-O—CH$_2$—CH(OR$_2$)—CH$_2$—;

D is C$_2$–C$_{12}$alkylene; C$_4$–C$_{50}$alkylene which is interrupted by oxygen; phenylene; biphenylene or phenylene-E-phenylene;

E is —O—; —S—; —SO$_2$—; —CH$_2$—; —CO—; or —C(CH$_3$)$_2$—;

R$_x$ is hydrogen; hydroxyl; C$_1$–C$_{20}$alkyl; C$_4$–C$_{12}$cycloalkyl; C$_1$–C$_{20}$alkoxy; C$_4$–C$_{12}$cycloalkoxy; C$_4$–C$_{12}$cycloalkyl or C$_4$–C$_{12}$cycloalkoxy each of which is interrupted by oxygen; C$_6$–C$_{12}$aryl; pyridyl; pyrimidinyl; triazinyl; pyrrolyl; furyl; thiophenyl; quinolyl; —OR$_z$; NHR$_z$; R$_z$; CONR'R''; C$_2$–C$_{20}$alkenyl; C$_4$–C$_{12}$cycloalkenyl which is interrupted by oxygen; C$_3$–C$_{20}$-alkynyl; or is any of the above alkyl, cycloalkyl, cycloalkenyl, alkoxy, cycloalkoxy, oxygen interrupted cycloalkyl or cycloalkenyl or cycloalkyl, aryl, heteroaryl, alkynyl which substituted by hydroxyl, —NH$_2$, —NHR$_5$, —NR$_5$R'$_5$, where R'$_5$ is defined as R$_5$ above, halogen C$_1$–C$_{20}$alkyl, C$_1$–C$_{20}$alkoxy, C$_4$–C$_{12}$cycloalkyl, C$_4$–C$_{12}$cycloalkoxy, C$_2$–C$_{20}$alkenyl, C$_4$–C$_{12}$cycloalkyl, C$_3$–C$_{20}$alkynyl, C$_6$–C$_{12}$aryl, C$_2$–C$_{18}$acylamino, C$_2$–C$_{18}$acyloxy, carboxyl, acryloxy, acrylamino, methacryloxy, methacrylamino,

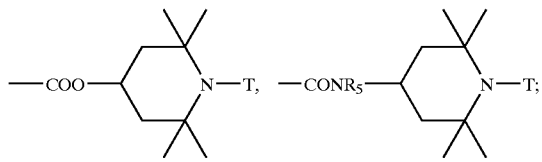

$R_y$ is hydrogen; $C_1$–$C_{20}$alkyl; $C_4$–$C_{12}$cycloalkyl; $C_4$–$C_{12}$cycloakyl which is interrupted by oxygen; $C_6$–$C_{12}$aryl; pyridyl; pyrimidinyl; triazinyl; pyrrolyl; furyl; thiophenyl; quinolyl; $R_z$; $C_2$–$C_{20}$alkenyl; $C_4$–$C_{12}$-cycloalkenyl; $C_4$–$C_{12}$-cycloalkenyl which is interrupted by oxygen; or $C_3$–$C_{20}$alkynyl; or is any of the above alkyl, cycloalkyl, aryl, hetero-aryl, alkenyl, cycloalkenyl or alkenyl, which substituted by hydroxyl, —$NH_2$, —$NHR_5$, —$NR_5R'_5$, where $R'_5$ is defined as $R_5$ above, halogen $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$aryl, $C_2$–$C_{18}$acylamino, $C_2$–$C_{18}$acyloxy, carboxyl, acryloxy, acrylamino, methacryloxy, methacrylamino,

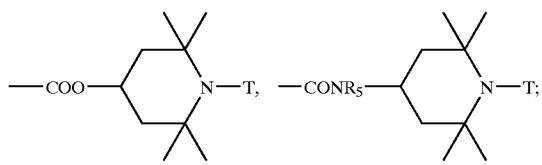

$R_z$ is —COR'; —COOR'; —CONR'R''; —CO—CH=$CH_2$; —CO—C($CH_3$)=$CH_2$;

R' and R'' independently of one another are hydrogen; $C_1$–$C_{20}$alkyl; $C_4$–$C_{50}$alkyl which is interrupted by oxygen; $C_4$–$C_{12}$cycloalkyl which is interrupted by oxygen; $C_2$–$C_{20}$alkenyl $C_4$–$C_{20}$alkenyl which is interrupted by oxygen; or $C_6$–$C_{12}$aryl; or are any of the above alkyl, O-interrupted alkyl, cycloalkyl, O-interrupted cycloalkyl, alkenyl O-interrupted alkenyl, aryl, which substituted by hydroxyl, —$NH_2$, —$NHR_5$, —$NR_5R'_5$, where $R'_5$ is defined as $R_5$ above, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$aryl, $C_2$–$C_{18}$acylamino, $C_2$–$C_{18}$acyloxy, carboxyl, acryloxy, acrylamino, methacryloxy, methacrylamino,

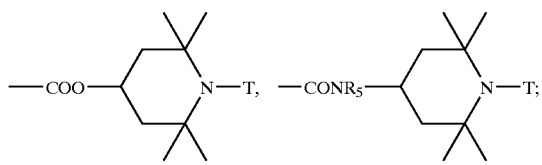

and with the proviso that the compound 2-(2hydroxyphenyl)-4-phenyl-6-(1-biphenyl)-1,3,5-triazine is not included; and with the proviso that if q is 0, $R_{12}$ and $R_{13}$ are not hydroxyl or allyloxy.

2. A composition according to claim 1, containing from 0.01 to 15 parts by weight of component (B) per 100 parts by weight of component (A).

3. A composition according to claim 1, comprising in addition to components (A) and (B) one or more other stabilizers or other additives.

4. A composition according to claim 1, comprising as component (A) a synthetic organic polymer.

5. A composition according to claim 1, comprising as component (A) a thermoplastic polymer, a binder for coatings or a photographic material.

6. A composition according to claim 5, comprising as additional component, one or more stabilizers selected from the group consisting of the sterically hindered amine and the 2-hydroxyphenyl-2H-benzotriazole light stabilizers.

7. A process for stabilizing organic material against damage by light, oxygen and/or heat, which process comprises adding to said material a stabilizer comprising one or more biphenyl-substituted triazine compounds of formula (1) or (1a)

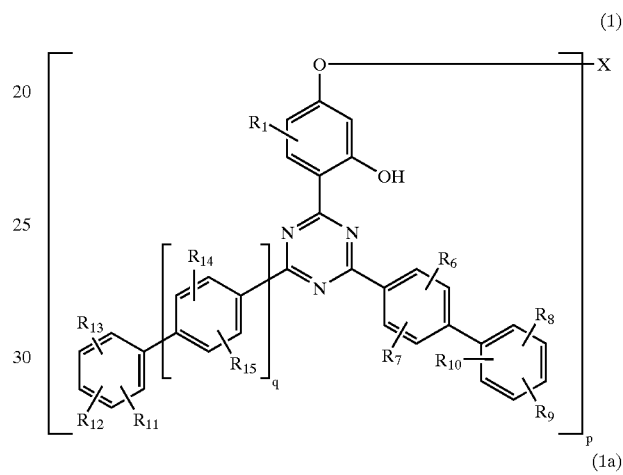

(1)

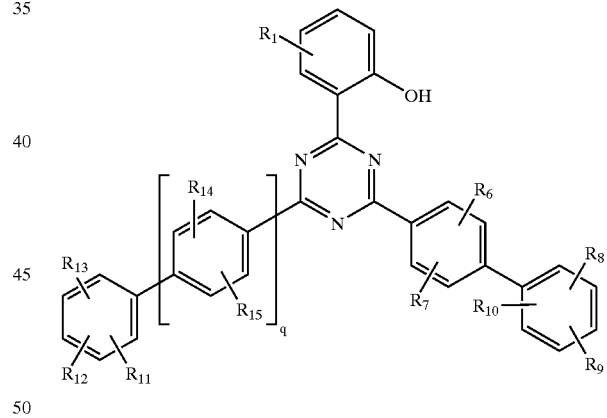

(1a)

where $R_1$ is hydrogen; $C_1$–$C_{24}$alkyl or $C_5$–$C_{12}$cycloalkyl; or $R_1$ is $C_1$–$C_{24}$alkyl or $C_5$–$C_{12}$cycloalkyl, each of which is substituted by halogen, —$R_4$, —$OR_5$, —$N((R_5)_2$, =$NR_5$, =O, —$CON(R_5)_2$, —$COR_5$, —$COOR_5$, —$OCOR_5$, —$OCON(R_5)_2$; —CN, —$NO_2$, —$SR_5$, —$SOR_5$, —$SO_2R_5$, —$P(O)(OR_5)_2$, a morpholinyl, piperidyl, 2,2,6,6-tetramethylpiperidyl, piperazinyl or N-methylpiperazinyl-group, or combinations thereof; and/or $R_1$ is $C_1$–$C_{24}$alkyl or $C_5$–$C_{12}$cycloalkyl which is interrupted by 1 to 6 phenylene, —O—, —$NR_5$—, —$CONR_5$—, —COO—, —OCO—, —$CH(R_5)$—, —$C(R_5)_2$— or —CO— groups or combinations thereof; $C_2$–$C_{24}$alkenyl; halogen; —$SR_3$, $SOR_3$; $SO_2R_3$; —$SO_3H$; —$SO_3M$; or a radical of the formula

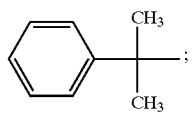

$R_3$ is $C_1$–$C_{20}$alkyl; $C_3$–$C_{18}$alkenyl; $C_5$–$C_{12}$cycloalkyl; $C_7$–$C_{15}$phenylalkyl, or $C_6$–$C_{12}$aryl which is unsubstituted or substituted by 1 to 3 $C_1$–$C_4$alkyl groups;

$R_4$ is $C_6$–$C_{12}$aryl; or $C_6$–$C_{12}$aryl which is substituted by halogen, $C_1$–$C_8$alkyl or $C_1$–$C_8$alkoxy or combinations thereof; $C_5$–$C_{12}$cycloalkyl; unsubstituted $C_7$–$C_{15}$phenylalkyl; or $C_7$–$C_{15}$phenylalkyl which is substituted in the phenyl ring by 1 to 3 halogen atoms, $C_1$–$C_8$alkyl, $C_1$–$C_8$alkoxy or combinations thereof or $C_2$–$C_8$alkenyl;

$R_5$ is $R_4$; hydrogen; $C_1$–$C_{24}$alkyl; or a radical of the formula

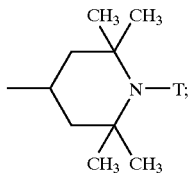

T is hydrogen; $C_1$–$C_8$alkyl; $C_2$–$C_8$alkyl which is substituted by hydroxyl or acyloxy; oxyl; hydroxyl; —$CH_2CN$; $C_1$–$C_{18}$alkoxy; $C_5$–$C_{12}$cycloalkoxy; $C_3$–$C_6$alkenyl; $C_7$–$C_9$phenylalkyl; $C_7$–$C_9$phenylalkyl which is substituted one, two or three times in the phenyl ring by $C_1$–$C_4$alkyl; or aliphatic $C_1$–$C_8$alkanoyl;

$R_6$ to $R_{15}$ independently of one another are hydrogen; hydroxyl; —C≡N; $C_1$–$C_{20}$alkyl; $C_1$–$C_{20}$alkoxy; phenyl-$C_1$–$C_{20}$alkoxy; $C_7$–$C_{20}$phenylalkyl; $C_4$–$C_{12}$cycloalkyl; $C_4$–$C_{12}$cycloalkoxy; halogen; halo-$C_1$–$C_5$alkyl; carboxyl; acylamino; acyloxy; $C_1$–$C_{12}$alkoxycarbonyl; aminocarbonyl; —O—Y; or O-Z; or $R_{11}$ and $R_{12}$, together with the phenyl radical, form a cyclic radical containing 2 to 4 carbon atoms which is interrupted by oxygen or —$NR_5$—.

M is alkali metal;

p 1 or 2;

q 0 or 1;

if p is 1,

X, Y and Z, independently of one another are hydrogen; $C_3$–$C_{50}$alkyl which is interrupted by oxygen and/or substituted by $R_2$ or $OR_2$; $((CH_2)_m$—$CH_2$—O—$)_n$—$R_2$; —$(CH_2$—$CH((CH_2)_{m\_R2})$—O—$)_{n\_R'2}$; —$(CH((CH_2)_m$—$R_2)$—$CH_2$—O—$)_n$—$R'_2$; —$(CH_2)_n$—$R_2$;

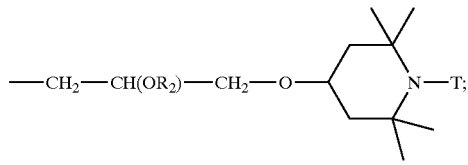

-continued

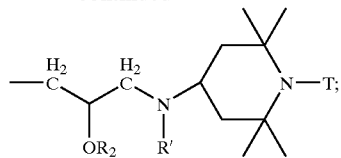

$C_4$–$C_{12}$cycloalkyl which is substituted by $R_2$; —$OR_2$-substituted $C_4$–$C_{12}$cycloalkyl; —$CH((CH_2)_n$—$R_2)$—CO—O—$(CH_2)_m$—$R'_2$; —$CH((CH_2)_n$—$R_2)$—CO—(NR')—$(CH_2)_m$—$R'_2$; —CO—$(CH_2)_n$—$R_2$; —CO—O—$(CH_2)_n$—$R_2$; —$CH_2$—CH(—O(CO)—$R_2)$—$R'_2$, —CO—NR'—$(CH_2)_n$—$R_2$; $C_6$–$C_{12}$aryl; allyl; $C_4$–$C_{20}$alkenyl; $C_4$–$C_{20}$alkenyl which is interrupted by oxygen; $C_4$–$C_{12}$cycloalkenyl; $C_4$–$C_{12}$cycloalkynyl; which is interrupted by oxygen; or $C_3$–$C_{20}$alkynyl;

$R_2$ and $R'_2$ independently of one another are $R_x$ if attached to a carbon atom and are $R_y$ if attached to an atom other than carbon;

n 0 to 20;

m 0 to 20;

and, if p is 2,

Y and Z, independently of one another are as defined for when p is 1; and

X is $C_2$–$C_{12}$alkylene; —CO—$(C_2$–$C_{12}$alkylene)—CO—; —CO-phenylene-CO—; CO-biphenylene-CO—; CO—O—$(C_2$–$C_{12}$alkylene)—O—CO—; —CO—O-phenylene-O—CO—; —CO—O-biphenylene-O—CO—; —CO—NR'—$(C_2$–$C_{12}$alkylene)—NR'—CO—; —CO—NR'-phenylene-NR'—CO—; —CO—NR'-biphenylene-NR'—CO—; —$CH_2$—CH(OH)—$CH_2$—; —$CH_2$—CH($OR_2$)—$CH_2$—; —$CH_2$—CH(OH)—$CH_2$—O-D-O—$CH_2$—CH(OH)—$CH_2$; —$CH_2$—CH($OR_2$)—$CH_2$—O-D-O—$CH_2$—CH($OR_2$)—$CH_2$—;

D is $C_2$–$C_{12}$alkylene; $C_4$–$C_{50}$alkylene which is interrupted by oxygen; phenylene; biphenylene or phenylene-E-phenylene;

E is —O—; —S—; —$SO_2$—; —$CH_2$—; —CO—; or —$C(CH_3)_2$—;

$R_x$ is hydrogen; hydroxyl; $C_1$–$C_{20}$alkyl; $C_4$–$C_{12}$cycloalkyl; $C_1$–$C_{20}$alkoxy; $C_4$–$C_{12}$cycloalkoxy; $C_4$–$C_{12}$cycloalkyl or $C_4$–$C_{12}$cycloalkoxy each of which is interrupted by oxygen; $C_6$–$C_{12}$aryl; pyridyl; pyrimidinyl; triazinyl; pyrrolyl; furyl; thiophenyl; quinolyl; —$OR_z$; $NHR_z$; $R_z$; CONR'R"; $C_2$–$C_{20}$alkenyl; $C_4$–$C_{12}$cycloalkenyl; $C_4$–$C_{12}$cycloalkenyl which is interrupted by oxygen; $C_3$–$C_{20}$alkynyl; or is any of the above alkyl, cycloalkyl, cycloalkenyl, alkoxy, cycloalkoxy, oxygen interrupted cycloalkyl or cycloalkenyl or cycloalkoxy, aryl, heteroaryl, alkenyl or alkynyl which is substituted by hydroxyl, —$NH_2$, —$NHR_5$, —$NR_5R'_5$, where $R'_5$ is defined as $R_5$ above, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$aryl, $C_2$–$C_{18}$acylamino, $C_2$–$C_{18}$acyloxy, carboxyl, acryloxy, acrylamino, methacryloxy, methacrylamino,

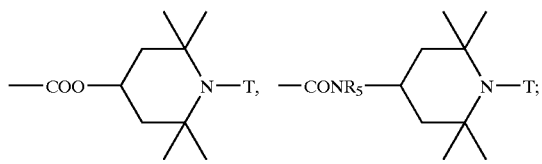

$R_y$ is hydrogen; $C_1$–$C_{20}$alkyl; $C_4$–$C_{12}$cycloalkyl which is interrupted by oxygen; $C_6$–$C_{12}$aryl; pyridyl; pyrimidinyl; triazinyl; pyrrolyl; furyl; thiophenyl; quinolyl; $R_z$; $C_2$–$C_{20}$alkenyl; $C_4$–$C_{12}$-cycloalkenyl; $C_4$–$C_{12}$-cycloalkenyl which is interrupted by oxygen; or $C_3$–$C_{20}$alkynyl; or is any of the above alkyl, cycloalkyl, aryl, hetero-aryl, alkenyl cicloalkenyl, or alkynyl, which substituted by hydroxyl, —$NH_2$, —$NHR_5$, —$NR_5R'_5$, where $R'_5$ is defined as $R_5$ above, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$aryl, $C_2$–$C_{18}$acylamino, $C_2$–$C_{18}$acyloxy, carboxyl, acryloxy, acrylamino, methacryloxy, methacrylamino,

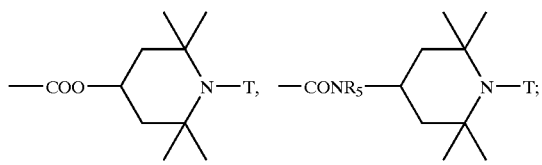

$R_z$ is —COR'; —COOR'; —CONR'R''; —CO—CH=$CH_2$; —CO—C($CH_3$)=$CH_2$;

R' and R'' independently of one another are hydrogen; $C_1$–$C_{20}$alkyl; $C_4$–$C_{50}$alkyl which is interrupted by oxygen; $C_4$–$C_{12}$cycloalkyl which is interrupted by oxygen; $C_2$–$C_{20}$alkenyl which is interrupted by oxygen; or $C_6$–$C_{12}$aryl; or are any of the above alkyl, O-interrupted alkyl, cycloalkyl, O-interrupted cycloalkyl, alkenyl O-interrupted alkenyl, aryl, which substituted by hydroxyl, —$NH_2$, —$NHR_5$, —$NR_5R'_5$, where $R'_5$ is defined as $R_5$ above, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$aryl, $C_2$–$C_{18}$acylamino, $C_2$–$C_{18}$acyloxy, carboxyl, acryloxy, acrylamino, methacryloxy, methacrylamino,

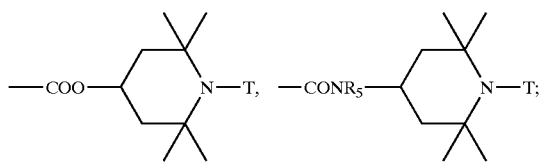

and with the proviso that the compound 2-(2hydroxyphenyl)-4-phenyl-6-(1-biphenyl)-1,3,5-triazine is not included; and with the proviso that if q is 0, $R_{12}$ and $R_{13}$ are not hydroxyl or allyloxy.

8. A cosmetic preparation comprising at least one biphenyl-substituted triazine compound of formula (1) or (1a) and a cosmetically acceptable auxiliary, where the compounds of formula (1) or (1a) are

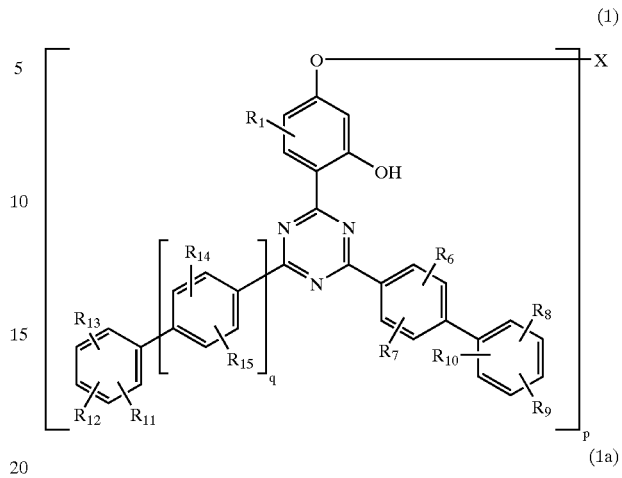

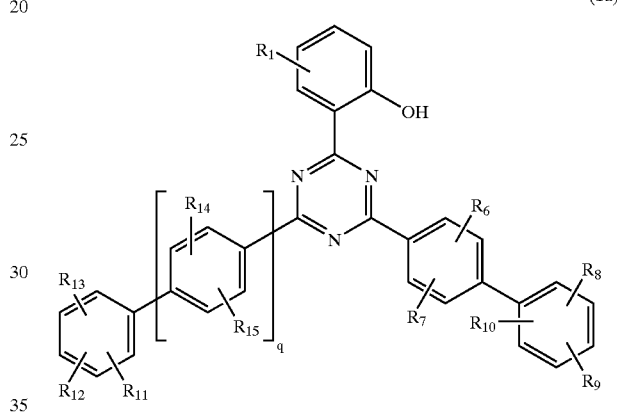

where $R_1$ is hydrogen; $C_1$–$C_{24}$alkyl or $C_5$–$C_{12}$cycloalkyl; or $C_1$–$C_{24}$alkyl or $C_5$–$C_{12}$cycloalkyl, each of which is substituted by halogen, —$R_4$, —$OR_5$, —$N((R_5)_2$, =$NR_5$, =O, —$CON(R_5)_2$, —$COR_5$, —$COOR_5$, —$OCOR_5$, —$OCON(R_5)_2$; —CN, —$NO_2$, —$SR_5$, —$SOR_5$, —$SO_2R_5$, —$P(O)(OR_5)_2$, a morpholinyl, piperidyl, 2,2,6,6-tetramethylpiperidyl, piperazinyl or N-methylpiperazinyl-group, or combinations thereof; and/or $R_1$ is $C_1$–$C_{24}$alkyl or $C_5$–$C_{12}$cycloalkyl which is interrupted by 1 to 6 phenylene, —O—, —$NR_5$—, —$CONR_5$—, —COO—, —OCO—, —$CH(R_5)$—, —$C(R_5)_2$— or —CO— groups or combinations thereof; $C_2$–$C_{24}$alkenyl; halogen; —$SR_3$, $SOR_3$; $SO_2R_3$; —$SO_3H$; —$SO_3M$; or a radical of the formula

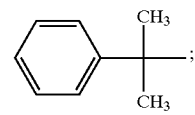

$R_3$ is $C_1$–$C_{20}$alkyl; $C_3$–$C_{18}$alkenyl; $C_5$–$C_{12}$cycloalkyl; $C_7$–$C_{15}$phenylalkyl, or $C_8$–$C_{12}$aryl which is unsubstituted or substituted by 1 to 3 $C_1$–$C_4$alkyl groups;

$R_4$ is $C_8$–$C_{12}$aryl; or $C_6$–$C_{12}$aryl which is substituted by halogen, $C_1$–$C_8$alkyl or $C_1$–$C_8$alkoxy or combinations thereof; $C_5$–$C_{12}$cycloalkyl; $C_7$–$C_{15}$-phenylalkyl; or $C_7$–$C_{15}$phenylalkyl which is substituted in the phenyl ring by 1 to 3 halogen atoms, $C_1$–$C_8$alkyl, $C_1$–$C_8$alkoxy or combinations thereof or $C_2$–$C_8$alkenyl;

$R_5$ is $R_4$; hydrogen; $C_1$–$C_{24}$alkyl; or a radical of the formula

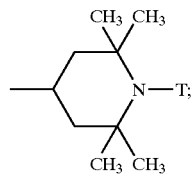

T is hydrogen; $C_1$–$C_8$alkyl; $C_2$–$C_8$alkyl which is substituted by hydroxyl or acyloxy; oxyl; hydroxyl; —CH$_2$CN; $C_1$–$C_{18}$alkoxy; $C_5$–$C_{12}$cycloalkoxy; $C_3$–$C_6$alkenyl; $C_7$–$C_9$phenylalkyl; $C_7$–$C_9$phenylalkyl which is substituted one, two or three times in the phenyl ring by $C_1$–$C_4$alkyl; or aliphatic $C_1$–$C_8$alkanoyl;

$R_6$ to $R_{15}$ independently of one another are hydrogen; hydroxyl; —C≡N; $C_1$–$C_{20}$alkyl; $C_1$–$C_{20}$alkoxy; phenyl-$C_1$–$C_{20}$alkoxy; $C_7$–$C_{20}$phenylalkyl; $C_4$–$C_{12}$cycloalkyl; $C_4$–$C_{12}$cycloalkoxy; halogen; halo-$C_1$–$C_5$alkyl; carboxyl; acylamino; acyloxy; $C_1$–$C_{12}$alkoxycarbonyl; aminocarbonyl; —O—Y; or O-Z; or $R_{11}$ and $R_{12}$, together with the phenyl radical, form a cyclic radical containing 2 to 4 carbon atoms which is interrupted by oxygen or —NR$_5$—.

M is alkali metal;

p 1 or 2;

q 0 or 1;

if p is 1,

X, Y and Z, independently of one another are hydrogen; $C_3$–$C_{50}$alkyl which is interrupted by oxygen and/or substituted by $R_2$ or OR$_2$; ((CH$_2$)$_m$—CH$_2$—O—)$_n$—R$_2$; —(CH$_2$—CH((CH$_2$)$_{m-R2}$)—O—)$_{n-R'2}$; —(CH((CH$_2$)$_m$—R$_2$)—CH$_2$—O—)$_n$—R'$_2$; —(CH$_2$)$_n$—R$_2$;

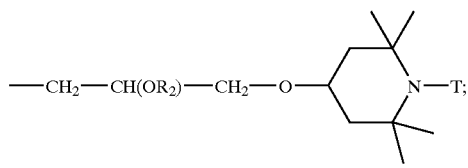

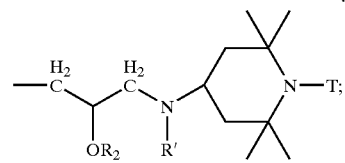

$C_4$–$C_{12}$cycloalkyl which is substituted by $R_2$; —OR$_2$-substituted $C_4$–$C_{12}$cycloalkyl; —CH((CH$_2$)$_n$—R$_2$)—CO—O—(CH$_2$)$_m$—R'$_2$; —CH((CH$_2$)$_n$—R$_2$)—CO—(NR')—(CH$_2$)$_m$—R'$_2$; —CO—(CH$_2$)$_n$—R$_2$; —CO—O—(CH$_2$)$_n$—R$_2$; —CH$_2$—CH(—O(CO)—R$_2$)—R'$_2$; —CO—NR'—(CH$_2$)$_n$—R$_2$; $C_6$–$C_{12}$aryl; allyl; $C_4$–$C_{20}$alkenyl; $C_4$–$C_{20}$alkenyl which is interrupted by oxygen; $C_4$–$C_{12}$cycloalkenyl; $C_4$–$C_{12}$cycloalkynyl; which is interrupted by oxygen; or $C_3$–$C_{20}$alkynyl;

$R_2$ and R'$_2$ independently of one another are $R_x$ if attached to a carbon atom and are $R_y$ if attached to an atom other than carbon;

n 0 to 20;

m 0 to 20;

and, if p is 2,

Y and Z, independently of one another are as defined for when p is 1; and

X is $C_2$–$C_{12}$alkylene; —CO—(C$_2$–C$_{12}$alkylene)—CO—; —CO-phenylene-CO—; CO-biphenylene-CO—; CO—O—(C$_2$–C$_{12}$alkylene)—O—CO—; —CO—O-phenylene-O—CO—; —CO—O-biphenylene-O—CO—; —CO—NR'—(C$_2$–C$_{12}$alkylene)—NR'—CO—; —CO—NR'-phenylene-NR'—CO—; —CO—NR'-biphenylene-NR'—CO—; —CH$_2$—CH(OH)—CH$_2$—; —CH$_2$—CH(OR$_2$)—CH$_2$—; —CH$_2$—CH(OH)—CH$_2$—O-D-O—CH$_2$—CH(OH)—CH$_2$; —CH$_2$—CH(OR$_2$)—CH$_2$—O-D-O—CH$_2$—CH(OR$_2$)—CH$_2$—;

D is $C_2$–$C_{12}$alkylene; $C_4$–$C_{50}$alkylene which is interrupted by oxygen; phenylene; biphenylene or phenylene-E-phenylene;

E is —O—; —S—; —SO$_2$—; —CH$_2$—; —CO—; or —C(CH$_3$)$_2$—;

$R_x$ is hydrogen; hydroxyl; $C_1$–$C_{20}$alkyl; $C_4$–$C_{12}$cycloalkyl; $C_1$–$C_{20}$alkoxy; $C_4$–$C_{12}$cycloalkoxy; $C_4$–$C_{12}$cycloalkyl or $C_4$–$C_{12}$cycloalkoxy each of which is interrupted by oxygen; $C_6$–$C_{12}$aryl; pyridyl; pyrimidinyl; triazinyl; pyrrolyl; furyl; thiophenyl; quinolyl; —OR$_z$; NHR$_z$; R$_z$; CONR'R"; $C_2$–$C_{20}$alkenyl; $C_4$–$C_{12}$cycloalkenyl; $C_4$–cycloalkenyl which is interrupted by oxygen; $C_3$–$C_{20}$alkynyl; or is any of the above alkyl, cycloalkyl, cycloalkenyl, alkoxy, cycloalkoxy, oxygen interrupted cycloalkyl or cycloalkenyl or cycloalkoxy, aryl, heteroaryl, alkenyl or alkynyl which is substituted by hydroxyl, —NH$_2$, —NHR$_5$, —NR$_5$R'$_5$, where R'$_5$ is defined as $R_5$ above, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$aryl, $C_2$–$C_{18}$acylamino, $C_2$–$C_{18}$acyloxy, carboxyl, acryloxy, acrylamino, methacryloxy, methacrylamino,

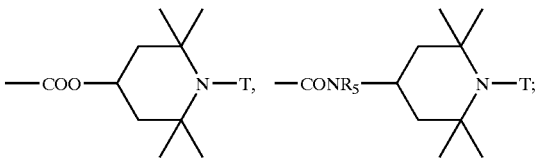

$R_y$ is hydrogen; $C_1$–$C_{20}$alkyl; $C_4$–$C_{12}$cycloalkyl; $C_4$–$C_{12}$cycloalkyl which is interrupted by oxygen; $C_6$–$C_{12}$aryl; pyridyl; pyrimidinyl; triazinyl; pyrrolyl; furyl; thiophenyl; quinolyl; R$_z$; $C_2$–$C_{20}$alkenyl; $C_4$–$C_{12}$-cycloalkenyl; $C_4$–$C_{12}$-cycloalkenyl which is interrupted by oxygen; or $C_3$–$C_{20}$alkynyl; or is any of the above alkyl, cycloakyl, aryl, hetero-aryl, alkenyl, cycloakyenyl or alkynyl, which is substituted by hydroxyl, —NH$_2$, —NHR$_5$, —NR$_5$R'$_5$, where R'$_5$ is defined as $R_5$ above, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$aryl, $C_2$–$C_{18}$acylamino, $C_2$–$C_{18}$acyloxy, carboxyl, acryloxy, acrylamino, methacryloxy, methacrylamino,

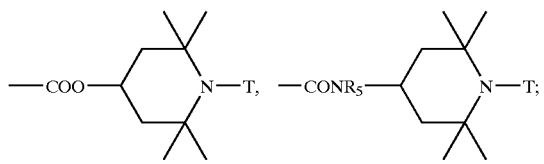

$R_z$ is —COR'; —COOR'; —CONR'R"; —CO—CH=CH$_2$; —CO—C(CH$_3$)=CH$_2$;

R' and R" independently of one another are hydrogen; $C_1$–$C_{20}$alkyl; $C_4$–$C_{50}$alkyl which is interrupted by oxygen; $C_4$–$C_{12}$cycloalkyl which is interrupted by oxygen; $C_2$–$C_{20}$alkenyl; $C_2$–$C_{20}$alkenyl which is interrupted by oxygen; or $C_6$–$C_{12}$aryl; or are any of the above alkyl, O-interrupted alkyl, cycloalkyl, O-interrupted cycloalkyl, alkenyl O-interrupted alkenyl, aryl, which substituted by hydroxyl, —NH$_2$, —NHR$_5$, —NR$_5$R'$_5$, where R'$_5$ is defined as R$_5$ above, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$aryl, $C_2$–$C_{18}$acylamino, $C_2$–$C_{18}$acyloxy, carboxyl, acryloxy, acrylamino, methacryloxy, methacrylamino,

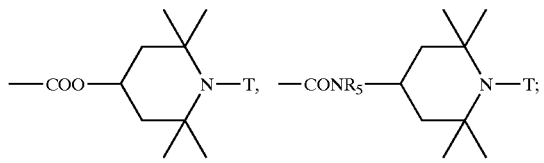

and with the proviso that the compound 2-(2hydroxyphenyl)-4-phenyl-6-(1-biphenyl)-1,3,5-triazine is not included; and with the proviso that if q is 0, R$_{12}$ and R$_{13}$ are not hydroxyl or allyloxy.

9. A process for protecting human skin against the damaging effect of sunlight, which process comprises applying a biphenyl-substituted triazine compound of formula (1) or (1a) to the skin, where the compounds of formula (1) or (1a) are (1)

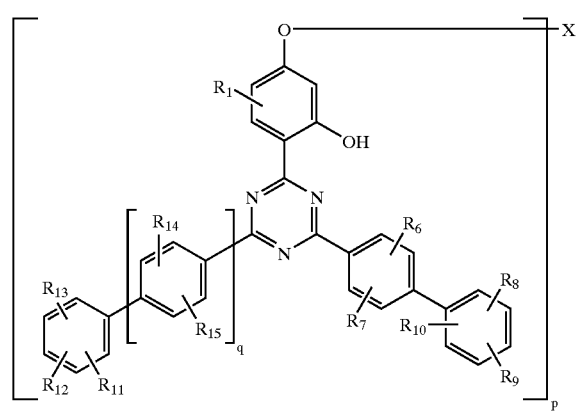

(1a)

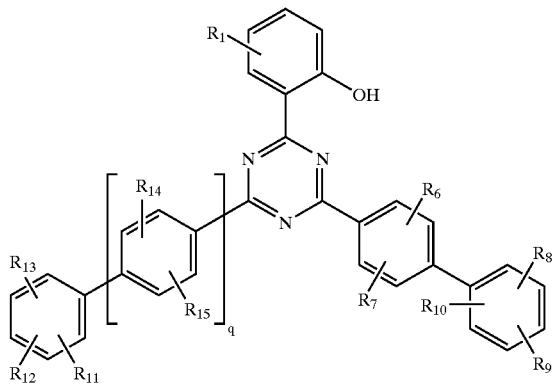

where
R$_1$ is hydrogen; $C_1$–$C_{24}$alkyl or $C_5$–$C_{12}$cycloalkyl; or R$_1$ is $C_1$–$C_{24}$alkyl or $C_5$–$C_{12}$cycloalkyl, each of which is substituted by halogen, —R$_4$, —OR$_5$, —N((R$_5$)$_2$, =NR$_5$, =O, —CON(R$_5$)$_2$, —COR$_5$, —COOR$_5$, —OCOR$_5$, —OCON(R$_5$)$_2$; —CN, —NO$_2$, —SR$_5$, —SOR$_5$, —SO$_2$R$_5$, —P(O)(OR$_5$)$_2$, a morpholinyl, piperidyl, 2,2,6,6-tetramethylpiperidyl, piperazinyl or N-methylpiperazinyl-group, or combinations thereof; and/or R$_1$ is $C_1$–$C_{24}$alkyl or $C_5$–$C_{12}$cycloalkyl which is interrupted by 1 to 6 phenylene, —O—, —NR$_5$—, —CONR$_5$—, —COO—, —OCO—, —CH(R$_5$)—, —C(R$_5$)$_2$— or —CO— groups or combinations thereof; $C_2$–$C_{24}$alkenyl; halogen; —SR$_3$, SOR$_3$; SO$_2$R$_3$; —SO$_3$H; —SO$_3$M; or a radical of the formula

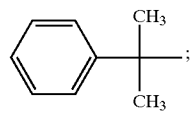

R$_3$ is $C_1$–$C_{20}$alkyl; $C_3$–$C_{18}$alkenyl; $C_5$–$C_{12}$cycloalkyl; $C_7$–$C_{15}$phenylalkyl; or $C_6$–$C_{12}$aryl which is unsubstituted or substituted by 1 to 3 $C_1$–$C_4$alkyl groups;

R$_4$ is $C_6$–$C_{12}$aryl; or $C_6$–$C_{12}$aryl which is substituted by halogen, $C_1$–$C_8$alkyl or $C_1$–$C_8$alkoxy or combinations thereof; $C_5$–$C_{12}$cycloalkyl; $C_7$–$C_{15}$phenylalkyl; or $C_7$–$C_{15}$phenylalkyl which is substituted in the phenyl ring by 1 to 3 halogen atoms, $C_1$–$C_8$alkyl, $C_1$–$C_8$alkoxy or combinations thereof or $C_2$–$C_8$alkenyl;

R$_5$ is R$_4$; hydrogen; $C_1$–$C_{24}$alkyl; or a radical of the formula

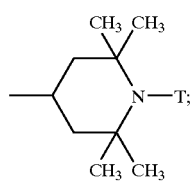

T is hydrogen; $C_1$–$C_8$alkyl; $C_2$–$C_8$alkyl which is substituted by hydroxyl or acyloxy; oxyl; hydroxyl; —CH$_2$CN; $C_1$–$C_{18}$alkoxy; $C_5$–$C_{12}$cycloalkoxy; $C_3$–$C_6$alkenyl; $C_7$–$C_9$phenylalkyl; $C_7$–$C_9$phenylalkyl which is substituted one, two or three times in the phenyl ring by $C_1$–$C_4$alkyl; or aliphatic $C_1$–$C_8$alkanoyl;

$R_6$ to $R_{15}$ independently of one another are hydrogen; hydroxyl; —C≡N; $C_1$–$C_{20}$alkyl; $C_1$–$C_{20}$alkoxy; phenyl-$C_1$–$C_{20}$alkoxy; $C_7$–$C_{20}$phenylalkyl; $C_4$–$C_{12}$cycloalkyl; $C_4$–$C_{12}$cycloalkoxy; halogen; halo-$C_1$–$C_5$alkyl; carboxyl; acylamino; acyloxy; $C_1$–$C_{12}$alkoxycarbonyl; aminocarbonyl; —O—Y; or O-Z; or $R_{11}$ and $R_{12}$, together with the phenyl radical, form a cyclic radical containing 2 to 4 carbon atoms which is interrupted by oxygen or —$NR_5$—.

M is alkali metal;

p 1 or 2;

q 0 or 1;

if p is 1,

X, Y and Z, independently of one another are hydrogen; $C_3$–$C_{50}$alkyl which is interrupted by oxygen and/or substituted by $R_2$ or $OR_2$; $((CH_2)_m—CH_2—O—)_n—R_2$; —$(CH_2—CH((CH_2)_{m—R2})—O—)_{n—R'2}$; —$(CH((CH_2)_m—R_2)—CH_2—O—)_n—R'_2$; —$(CH_2)_n—R_2$;

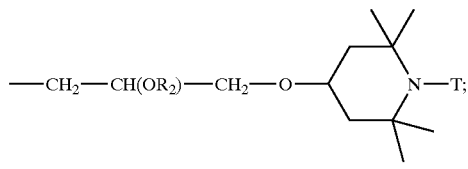

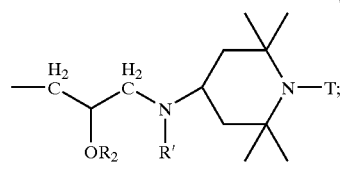

$C_4$–$C_{12}$cycloalkyl which is substituted by $R_2$; —$OR_2$-substituted $C_4$–$C_{12}$cycloalkyl; —$CH((CH_2)_n—R_2)$—CO—O—$(CH_2)_m$—$R'_2$; —$CH((CH_2)_n—R_2)$—CO—(NR')—$(CH_2)_m$—$R'_2$; —CO—$(CH_2)_n$—$R_2$; —CO—O—$(CH_2)_n$—$R_2$; —$CH_2$—CH(—O(CO)—$R_2$)—$R'_2$, —CO—NR'—$(CH_2)_n$—$R_2$; $C_6$–$C_{12}$aryl; allyl; $C_4$–$C_{20}$alkenyl; $C_4$–$C_{20}$alkenyl which is interrupted by oxygen; $C_4$–$C_{12}$cycloalkenyl; $C_4$–$C_{12}$cycloalkynyl; which is interrupted by oxygen; or $C_3$–$C_{20}$alkynyl;

$R_2$ and $R'_2$ independently of one another are $R_x$ if attached to a carbon atom and are $R_y$ if attached to an atom other than carbon;

n 0 to 20;

m 0 to 20;

and, if p is 2,

Y and Z, independently of one another are as defined for when p is 1; and

X is $C_2$–$C_{12}$alkylene; —CO—($C_2$–$C_{12}$alkylene)—CO—; —CO-phenylene-CO—; CO-biphenylene-CO—; CO—O—($C_2$–$C_{12}$alkylene)—O—CO—; —CO—O-phenylene-O—CO—; —CO—O-biphenylene-O—CO—; —CO—NR'—($C_2$–$C_{12}$alkylene)—NR'—CO—; —CO—NR'-phenylene-NR'—CO—; —CO—NR'-biphenylene-NR'—CO—; —$CH_2$—CH(OH)—$CH_2$—; —$CH_2$—CH($OR_2$)—$CH_2$—; —$CH_2$—CH(OH)—$CH_2$—O-D-O—$CH_2$—CH(OH)—$CH_2$; —$CH_2$—CH($OR_2$)—$CH_2$—O-D-O—$CH_2$—CH($OR_2$)—$CH_2$—;

D is $C_2$–$C_{12}$alkylene; $C_4$–$C_{50}$alkylene which is interrupted by oxygen; phenylene; biphenylene or phenylene-E-phenylene;

E is —O—; —S—; —$SO_2$—; —$CH_2$—; —CO—; or —$C(CH_3)_2$—;

$R_x$ is hydrogen; hydroxyl; $C_1$–$C_{20}$alkyl; $C_4$–$C_{12}$cycloalkyl; $C_1$–$C_{20}$alkoxy; $C_4$–$C_{12}$cycloalkoxy; $C_4$–$C_{12}$cycloalkyl or $C_4$–$C_{12}$cycloalkoxy each of which is interrupted by oxygen; $C_6$–$C_{12}$aryl; pyridyl; pyrimidinyl; triazinyl; pyrrolyl; furyl; thiophenyl; quinolyl; —$OR_z$; $NHR_z$; $R_z$; $CONR'R''$; $C_2$–$C_{20}$alkenyl; $C_4$–$C_{12}$cycloalkenyl; $C_4$–$C_{12}$cycloalkenyl which is interrupted by oxygen; $C_3$–$C_{20}$alkynyl; or is any of the above alkyl, cycloalkyl, cycloalkenyl, alkoxy, cycloalkoxy, oxygen interrupted cycloalkyl or cycloalkenyl or cycloalkoxy, aryl, heteroaryl, alkenyl or alkynyl which is substituted by hydroxyl, —$NH_2$, —$NHR_5$, —$NR_5R'_5$, where $R'_5$ is defined as $R_5$ above, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$aryl, $C_2$–$C_{18}$acylamino, $C_2$–$C_{18}$acyloxy, carboxyl, acryloxy, acrylamino, methacryloxy, methacrylamino,

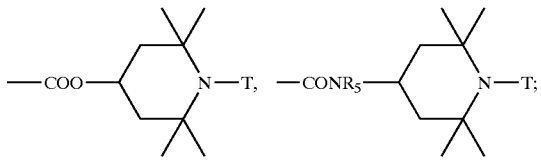

$R_y$ is hydrogen; $C_1$–$C_{20}$alkyl; $C_4$–$C_{12}$cycloalkyl which is interrupted by oxygen; $C_6$–$C_{12}$aryl; pyridyl; pyrimidinyl; triazinyl; pyrrolyl; furyl; thiophenyl; quinolyl; $R_z$; $C_2$–$C_{20}$alkenyl; $C_4$–$C_{12}$-cycloalkenyl; $C_4$–$C_{12}$-cycloalkenyl which is interrupted by oxygen; or $C_3$–$C_{20}$alkynyl; or is any of the above alkyl, cycloalkyl, aryl, hetero-aryl, alkenyl cicloalkenyl or alkynyl, which is substituted by hydroxyl, —$NH_2$, —$NHR_5$, —$NR_5R'_5$, where $R'_5$ is defined as $R_5$ above, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$aryl, $C_2$–$C_{18}$acylamino, $C_2$–$C_{18}$acyloxy, carboxyl, acryloxy, acrylamino, methacryloxy, methacrylamino,

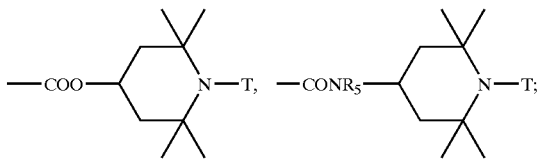

$R_z$ is —COR'; —COOR'; —CONR'R''; —CO—CH=$CH_2$; —CO—$C(CH_3)$=$CH_2$;

R' and R'' independently of one another are hydrogen; $C_1$–$C_{20}$alkyl; $C_4$–$C_{50}$alkyl which is interrupted by oxygen; $C_4$–$C_{12}$cycloalkyl; $C_4$–$C_{12}$cycloalkyl which is interrupted by oxygen; $C_2$–$C_{20}$alkenyl; $C_4$–$C_{20}$alkenyl which is interrupted by oxygen; or $C_6$–$C_{12}$aryl; or are any of the above alkyl, O-interrupted alkyl, cycloalkyl, O-interrupted cycloalkyl, alkenyl O-interrupted alkenyl, aryl, which is substituted by hydroxyl, —$NH_2$, —$NHR_5$, —$NR_5R'_5$, where $R'_5$ is defined as $R_5$ above, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$aryl, $C_2$–$C_{18}$acylamino, $C_2$–$C_{18}$acyloxy, carboxyl, acryloxy, acrylamino, methacryloxy, methacrylamino,
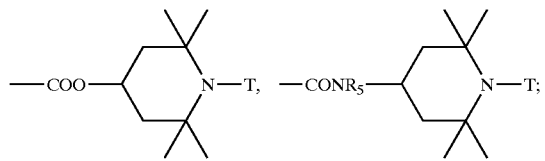
and
with the proviso that the compound 2-(2hydroxyphenyl)-4-phenyl-6-(1-biphenyl)-1,3,5-triazine is not included; and
with the proviso that if q is 0, $R_{12}$ and $R_{13}$ are not hydroxyl or allyloxy.
* * * * *